US012226540B2

(12) United States Patent
Bernthal

(10) Patent No.: US 12,226,540 B2
(45) Date of Patent: Feb. 18, 2025

(54) PARTICLE SIZE AND WETNESS REDUCTION DEVICES FOR FOG GENERATING EQUIPMENT

(71) Applicant: D. P. Tyson Bernthal, St. Augustine, FL (US)

(72) Inventor: D. P. Tyson Bernthal, St. Augustine, FL (US)

(73) Assignee: D. P. Tyson Bernthal, St. Augustine, FL (US)

( * ) Notice: Subject to any disclaimer, the term of this patent is extended or adjusted under 35 U.S.C. 154(b) by 0 days.

(21) Appl. No.: 18/233,319

(22) Filed: Aug. 13, 2023

(65) Prior Publication Data

US 2024/0285824 A1 Aug. 29, 2024

Related U.S. Application Data

(60) Provisional application No. 63/460,868, filed on Apr. 20, 2023, provisional application No. 63/446,367, filed on Feb. 17, 2023.

(51) Int. Cl.

| | |
|---|---|
| ***B01D 45/08*** | (2006.01) |
| ***A61L 2/22*** | (2006.01) |
| *B05B 7/00* | (2006.01) |
| *B05B 7/24* | (2006.01) |
| *B05B 17/06* | (2006.01) |

(52) U.S. Cl.

CPC ................ *A61L 2/22* (2013.01); *B01D 45/08* (2013.01); *A61L 2202/11* (2013.01); *A61L 2202/15* (2013.01); *A61L 2202/25* (2013.01); *B05B 7/0012* (2013.01); *B05B 7/2491* (2013.01); *B05B 17/0615* (2013.01)

(58) Field of Classification Search

CPC ........ B01D 45/08; A61L 2/22; A61L 2202/11; A61L 2202/15; A61L 2202/25; B05B 7/0012; B05B 7/2491; B05B 17/0615

USPC .......................................................... 239/500

See application file for complete search history.

(56) References Cited

U.S. PATENT DOCUMENTS 3,097,645 A * 7/1963 Lester .................... A61M 11/06 239/338
3,490,697 A * 1/1970 Best, Jr. .............. B05B 17/0615 310/318
3,561,444 A * 2/1971 Boucher .............. A61M 11/005 261/DIG. 65
3,790,079 A * 2/1974 Berglund ............ B05B 17/0607 366/115
3,834,682 A * 9/1974 McPhee ................ A61M 16/16 261/DIG. 65

(Continued)

*Primary Examiner* — Chee-Chong Lee

(74) *Attorney, Agent, or Firm* — John L. DeAngelis; Wolter Van Dyke Davis, PLLC

(57) ABSTRACT

An enclosed structure for receiving fog from a fog-producing device. The fog comprises fog particles of water and an active substance that is capable of being aerosolized. A plurality of spaced-apart redirector surfaces is located within the enclosed structure; these surfaces define flow paths for the fog to travel. The fog particles collide with or pass proximate the redirector surfaces, causing the larger fog particles to fall out of the fog flow path, while the smaller fog particles continue along the fog flow path, finally exiting the enclosed structure. After exiting, the fog particles strike a target, with the active substance within the fog particles treating the target.

21 Claims, 20 Drawing Sheets

(56) References Cited

U.S. PATENT DOCUMENTS

| | | | | |
|---|---|---|---|---|
| 4,031,171 | A * | 6/1977 | Asao .................. | B05B 17/0615<br>261/119.1 |
| 2008/0245362 | A1 * | 10/2008 | Moessis ............... | A61M 11/002<br>239/338 |
| 2014/0251320 | A1 * | 9/2014 | Giroux .................. | B05B 7/0869<br>128/200.21 |

* cited by examiner

1000

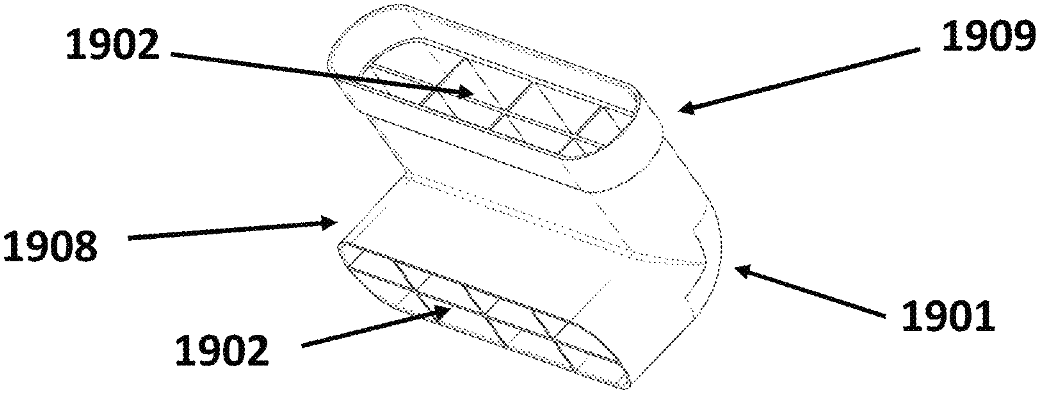
FIG. 19A
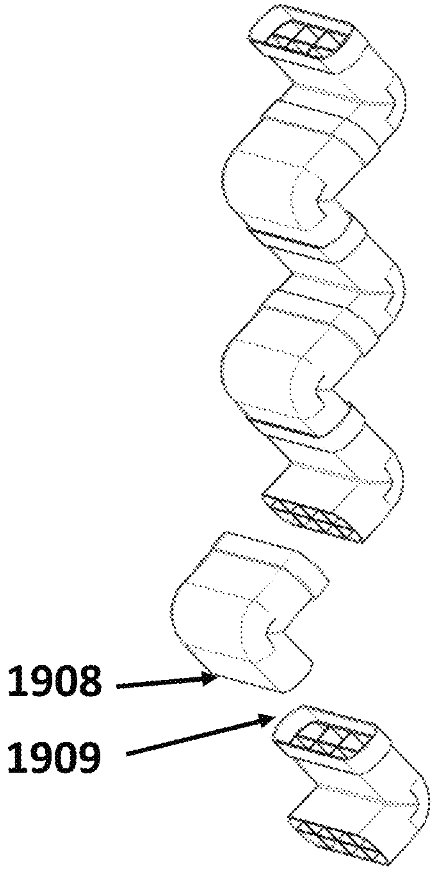
1900
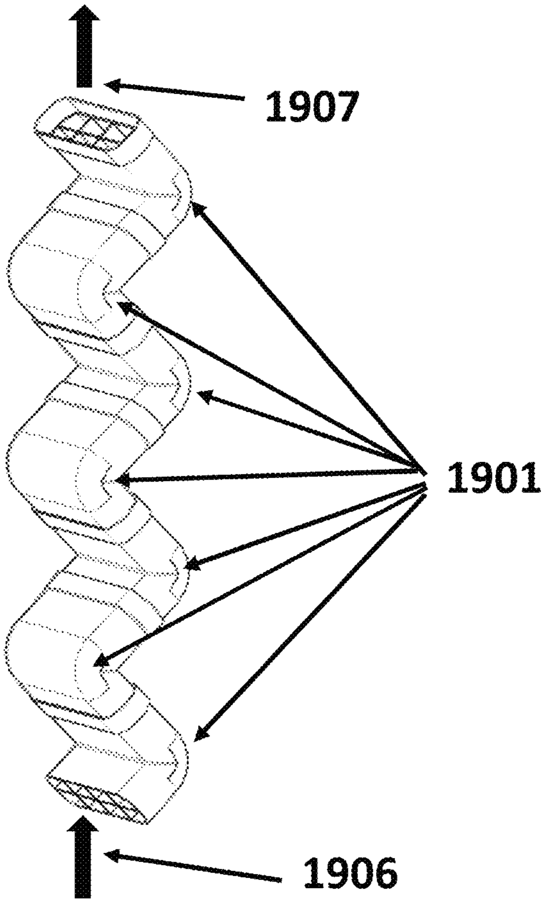
FIG. 19B FIG. 19C

PARTICLE SIZE AND WETNESS REDUCTION DEVICES FOR FOG GENERATING EQUIPMENT

CROSS REFERENCE TO RELATED APPLICATIONS

Under 35 U.S.C. § 119(e), this application claims benefit of the Provisional Application No. 63/446,367, filed Feb. 17, 2023, and the Provisional Application No. 63/460,868 filed on Apr. 20, 2023, the entire contents of both applications are incorporated by reference as if fully set forth herein.

BACKGROUND OF THE INVENTION

Nebulizers, humidifiers, thermal, cold and ultrasonic foggers create and emit into the environment or target area small water droplets that appear as fog (i.e., a substance dispersed or suspended in the air, especially one normally liquid or solid) or an aerosol (i.e., a suspension of tiny particles of liquid, solid or both within a gas).

Droplets produced by conventional foggers range in size from sub-micron to 50 microns or larger. For the purpose of this disclosure, droplets of 5 to 50 microns or larger (hereinafter referred to as “large(r) particle(s)” or “large(r) droplet(s)”) tend to be too large to be effective in certain applications as envisioned by the inventor. There are at least three primary disadvantages associated with these larger particle sizes. The first disadvantage relates to wetness, as the area around the fogging device becomes quite damp and in time, very wet. The second disadvantage relates to the incomplete and uneven distribution of the particles, creating inconsistencies in desired outcomes of various treatments. And the third disadvantage is the larger particles are incapable of fitting into the smaller cracks and crevices in surfaces and within fabrics needing treatment. These larger particles tend to block the path for smaller particles that attempt to fill those cracks and crevices.

These issues are hindrances to the efficacy of many desired applications. The product that is being fogged is not delivered to the hardest to reach and hidden locations (thus failing to achieve the desired effect) and is overdelivered to other areas creating “hotspots” of overtreatment. While creating these larger particles at 5 to 50 microns, the foggers simultaneously create smaller particles, many of which are sub-micron in size, but those particles tend to be overwhelmed by the larger particles and are very quickly absorbed by the larger particles. The result is a fog with an average micron size of 5 to 50 and growing greater with time as the large particles rapidly merge, altering the humidity and dew point and resulting in excessive wetness. This invention achieves the goal of reducing the number of large particles that exit the fogger so that these issues are avoided.

BRIEF DESCRIPTION OF THE FIGURES

The present invention can be more easily understood and the advantages and uses thereof more readily apparent when the detailed description of the present invention is read in conjunction with the figures wherein:

FIGS. 19A, 19B and 19C depict an oval/rectangular tube defining a plurality of individual channels that function as fog flow paths and redirector surfaces.

In accordance with common practice, the various described and illustrated features are not drawn to scale, but are drawn to emphasize specific characteristics relevant to the invention. Like reference numerals denote like elements throughout the figures and text.

DETAILED DESCRIPTION OF THE INVENTION

Figure 1:
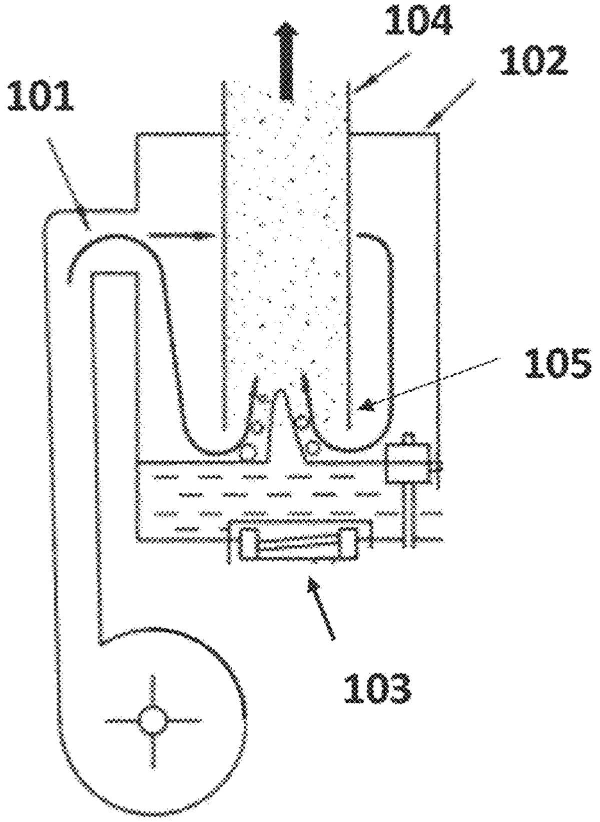
FIG. 1 depicts a prior art sonic fogger to which the teachings of the present invention can be applied.

For purposes of this disclosure, both vapors and aerosols, unless specifically stated otherwise, shall be considered synonymous and may be referred to as “aerosol(s)” or their colloquial name, “fog,” and shall mean a substance generated by a fogger or by another device, (such as a device for producing an aerosol or for producing a vapor, all of which are referred to herein as a fogger, a fogger machine, or a fog-producing device, etc.) and comprised of small particles in the nature of droplets (e.g., small water droplets) suspended in air and that appear as fog when emitted into the environment. The terms “particles” and “droplets” are also used herein interchangeably.

A primary object of the present invention is to provide an aerosol treatment apparatus for attachment to a variety of fogger machines, the apparatus being adapted to remove aerosol particles having a size greater than about 2.5 microns. Removal of these particles produces an aerosol capable of improved coverage of target surfaces within a given space as well as the unoccupied volume of the space itself. The apparatus works with aerosols created from both aqueous and inorganic and organic-based solutions.

For the purpose of this disclosure, the term "target" refers to any space or surface to be treated with the aerosol. This can be the interior surfaces of an enclosure, the space defined by the enclosure and/or objects within the enclosure. The modified aerosols of the subject invention are more effective than non-modified aerosols in penetrating porous surfaces, fabrics and cracks and crevices of objects, with reduced wetness over non-modified aerosols.

Thus, the invention thoroughly and evenly delivers any water-based product (or a liquid-based product of similar consistency) as a fog (generated by a fogger) for the purpose of making direct contact with the surfaces of a target(s) in an enclosed space. The concept is supported by recognizing that a product can have the desired effect on a target only if it makes direct contact with the target.

Another objective of the invention is to ensure that the fog product is capable of reaching every possible location in a room where the target(s) exist; in the air, on hard surfaces, within the pores of porous surfaces, within fabrics, and within otherwise unreachable cracks and crevices, without making the space overly wet, which would potentially cause damage to the target or target contents, or require an excessive clean-up process.

When the average particle size fog or an aerosol is less than about 2.5 microns, the fogged product stays suspended in a column of air for longer periods of time than do fogged products comprised of larger particles, and diffuses more evenly throughout a room, delivering the product to every location in that room. This ensures that targets in the air, on surfaces and deep within cracks and crevices will come in contact with the product that has been delivered in the form of fog. Large particles, averaging from 5 to 50 microns in size, have too much mass to be suspended in the air column and therefore precipitate to surfaces in the room or the room floor. Additionally, high humidity and increased dew point temperatures caused by the presence of such larger particles create heavy condensation and increased wetness.

As a key component to understanding how the invention produces these results, we first need to understand how extremely small droplets of a solution, a decontaminate solution, for example, behave when they are introduced into an enclosed space, how they remain suspended in the air rather than rapidly precipitating to the floor, and how they are evenly distributed (or nearly evenly distributed) through the room in a gas-like fashion.

The following discussion reveals those answers and explains the great benefits of introducing aerosol particles at a consistently small size to ensure rapid diffusion of those droplets, including into even the smallest cracks and crevices, in the room and the effects of the decontaminate solution. For the purpose of providing a consistent example we have chosen 1 micron as the particle size for the following explanations. However, those skilled in the art recognize that these equations can be extended to particles of any size and that particles of about 2.5 microns and less behave to the benefit of the invention.

Terminal Velocity of Suspended Droplets

Droplets diffused throughout the surrounding space have a settling time associated with the balance between gravity and drag on the falling droplet. Droplets suspended in the air can be analyzed using the creeping flow approximation which can be justified by calculating Reynolds number (Re) and verifying that it is much less than one (Re<<1). The goal is to calculate the terminal velocity of the droplet in air. The Reynolds number is a dimensionless parameter. Re depends only on the relative velocity between an object and the gas flow. Note that it is aerodynamically equivalent for air to flow past a stationary object, or for the object to move in stationary air. Laminar flow around a particle occurs when Re<<1. Within this region, viscous forces are much greater than inertial forces. This type of flow is characterized by a smooth pattern of streamlines that are symmetrical on the upstream and downstream sides of the object.

Using the following properties at T=77° F.:

1.

$$\rho_{air} = 1.293\ \frac{\text{kg}}{\text{m}^3}$$

2.

$$\mu_{air} = 1.81 \times 10^{-5}\ \frac{\text{kg}}{\text{m}\cdot\text{s}}\ \text{(viscosity)}$$

3.

$$\rho_{liquid} = 998\ \frac{\text{kg}}{\text{m}^3}\ \text{(water)}$$

4.

Droplet diameter = 1 micron

To calculate the terminal velocity, the Stokes drag force must exactly balance the effective downward force on the droplet which is equal to the sphere weight minus the buoyancy force.

The downward force due to the weight of the droplet is:

$$F_{weight} = \frac{4}{3}\pi\,\rho_{liquid}\,g\,a^3 \tag{1}$$

where a is the radius of the droplet.

The Stokes force on the droplet due to drag is given by:

$$F_{Stokes} = 6\pi\mu_{air}\,aV \tag{2}$$

where V is the velocity of the droplet.

The drag force opposes particle motion relative to the surrounding gas. Drag results from a number of mechanisms, including gas viscosity (friction) and the energy required by the particle to displace gas as it moves (inertia).

The buoyant force due to the buoyancy on the droplet from the air is given by:

$$F_{bouyant} = \frac{4}{3}\pi\rho_{air}\,g\,a^3 \tag{3}$$

Subtracting equation (3) from (1) and equating it to (2):

$$6\pi\mu_{air}\,aV = \frac{4}{3}\pi\,\rho_{liquid}\,g\,a^3 - \frac{4}{3}\pi\,\rho_{air}\,g\,a^3 \tag{4}$$

Rearranging to solve for the terminal velocity:

$$V = \frac{4a^2}{18\mu_{air}}(\rho_{liquid} - \rho_{air})g \tag{5}$$

The terminal velocity determines how long droplets will hang in the air and determines how long it will take the droplets to settle to the ground. The terminal velocity is a function of the square of the diameter of the droplet. The smaller the droplet, the smaller the terminal velocity which results in a larger hang time of the droplets which results in a longer time for all of the droplets to settle to the ground.

Substituting the values on the previous page:

$$V = \frac{4(0.5\times10^{-6})^2\ \mathrm{m}^2}{18\left(1.81\times10^{-5}\,\frac{\mathrm{kg}}{\mathrm{m\cdot s}}\right)}\left(998\,\frac{\mathrm{kg}}{\mathrm{m}^3} - 1.293\,\frac{\mathrm{kg}}{\mathrm{m}^3}\right)9.81\,\frac{\mathrm{m}}{\mathrm{s}^2} \tag{6}$$

Yields a terminal velocity of:

$$V = 3.002\times10^{-5}\,\frac{\mathrm{m}}{\mathrm{s}} \tag{7}$$

For a room with a ceiling height h=3 m, the time for a droplet close to the ceiling to fall to the floor is:

$$t = \frac{h}{V} = \frac{3\ \mathrm{m}}{3.002\times10^{-5}\,\frac{\mathrm{m}}{\mathrm{s}}} = 9.93\times10^4\ \mathrm{s} = 68\ \text{hours} \tag{8}$$

At a 1-micron particle diameter, the particles are close to neutrally buoyant. Verify that the Reynolds number is small enough that the creeping flow approximation is appropriate:

$$Re = \frac{2a\,\rho_{liquid}\,V}{\mu_{air}\,g} = \frac{2\,(0.5\times10^{-6}\ \mathrm{m})\,998\,\frac{\mathrm{kg}}{\mathrm{m}^3}\left(3.002\times10^{-5}\,\frac{\mathrm{m}}{\mathrm{s}}\right)}{\left(1.81\times10^{-5}\,\frac{\mathrm{kg}}{\mathrm{m\cdot s}}\right)} = 0.00167 \tag{9}$$

Since Re<<1. The creeping flow approximation is appropriate.

Tranquil and Stirred Settling

Knowing the velocity V allows an estimate to be made of how long it will take for a droplet to settle out of the air in a chamber or room. If there is no convective air motion within a room of height h, it will simply take a time of V×h for all droplets to settle out. If the droplet concentration n at a given point was measured, it would remain constant to a point, then abruptly fall to zero as the last particles settled past the point. If the droplets within the room were constantly stirred, droplets would still be lost through gravitational settling. However, the constant re-dispersal of droplets would lead to an exponentially decreasing concentration. In time dt the overall concentration would decrease by:

$$dn = \frac{n\,V}{h}dt \tag{10}$$

Integrating for the initial condition of $n=n_0$ at t=0 gives:

$$n(t) = n_0 e^{\left(\frac{-Vt}{h}\right)} \tag{11}$$

Diffusion of Droplets

Brownian motion is the random motion of a particle as a result of collisions with surrounding gaseous molecules. The physical process in which a substance tends to spread steadily from regions of high concentration to regions of lower concentration is called diffusion. Diffusion can therefore be considered a macroscopic manifestation of Brownian motion on the microscopic level. Particle Brownian motion leads to three characteristics of particle behavior that are analogous or similar to molecular behavior in an ideal gas-diffusion, mean velocity and mean free path. The Brownian motion of droplet particles leads to the bulk movement of particles through diffusion. As in the case of molecules, the flux of droplet particles moving from a high to low concentration region through diffusion is given by Fick's first law of diffusion:

$$J = -D\frac{dn}{dt} \tag{46}$$

where D is the particle diffusion coefficient and dn/dx the particle concentration gradient.

D can be derived from equating the Stokes drag force experienced by particles to the net force arising from molecular collisions.

As droplets are constantly exchanging energy with the surrounding gas molecules, they have the same kinetic energy as the molecules. Therefore, in the same way that the root mean square and arithmetic mean velocities for gas molecules were derived, the same quantities can be derived for the droplets:

$$\bar{c} = \sqrt{\frac{8hT}{\pi m}} = \sqrt{\frac{48\,kT}{\pi^2 \rho\, d^3}} \tag{47}$$

Particle mean free is not directly analogous to molecule mean free path. As most particles are much more massive than gas molecules, it takes many collisions to lead to a change in direction of particle motion. However, the concepts are similar. Particle mean free path is defined as the distance traveled before molecular collisions have led to a complete (i.e. 90°) Change in direction. This is essentially the stopping distance of the particles under the influence of Brownian motion, and is given by $$\lambda_p = \tau\bar{c} \tag{48}$$

The diffusion coefficient of a droplet can be expressed in terms of particle mean free path and mean velocity:

$$D = \frac{\pi}{8}\lambda_p\bar{c} \tag{49}$$

-continued $$D = \frac{\pi}{8}\tau\bar{c}^2 \tag{50}$$

Diffusion is not affected by the drag on the particle so that $C_D=1$ in equation (13):

$$D = \frac{\pi}{8}\left(\frac{\rho_{liquid}4a^2}{18\mu_{air}}\right)\left(\frac{48kT}{\pi^2\rho d^3}\right) \tag{51}$$

which yields:

$$D = \frac{kT}{3\pi\mu d} \tag{52}$$

where k is the Boltzmann constant and T the temperature of the air.

$$D = \frac{\left(1.38\times10^{-23}\frac{J}{K}\right)(300\text{K})}{3\pi\left(1.81\times10^{-5}\frac{\text{kg}}{m\cdot s}\right)(1\times10^{-6}\ \text{m})} \tag{53}$$

The diffusion coefficient for a 1-micron diameter droplet is:

$$D = 2.574\times10^{-11}\frac{m^2}{s}$$

The diffusion coefficient for a 1-micron diameter droplet is ten times faster than a 10-micron droplet. The sub-micron size droplets exhibit gas-like, diffusion and penetration properties.

Droplet Filtering by Abrupt Redirection of the Flow Stream Momentum

If you apply a steady force to a droplet, it will eventually reach a steady velocity as the drag force matches the applied force. The assumption was made earlier that this steady state is reached relatively rapidly. However, knowing something about how long a particle takes to respond and 'adjust' to a change in applied force is a very useful tool for determining behavior under conditions of change. The terminal velocity can therefore be written as $$V = \tau g \tag{12}$$

where $\tau$ has the units of time.

The quantity $\tau$ is referred to as Relaxation Time and is essentially a measure of how rapidly a particle will respond or 'relax' to any changes in applied force. $\tau$ occurs in many instances where a particle's motion is governed by mechanical mobility. It is useful for looking at how rapidly different particles will respond to a force resulting from a change in pressure—for instance, if a group of particles with different diameters are moving under the influence of a changing stream direction. The relaxation time is given by:

$$\tau = \frac{\rho_{liquid}4a^2C_D}{18\mu_{air}} \tag{13}$$

where $C_D$ is the drag coefficient due to Newtonian drag is given by:

$$C_D = \frac{24}{Re}$$

Substituting for the Reynolds Number Re shows that the drag coefficient is given by:

$$C_{D_1} = C_{D_2} = C_D = \frac{24}{Re} = \frac{24}{\frac{\rho_{liquid}V_SD_s}{\mu_{air}g}} \tag{14}$$

where $V_S$ is the velocity of the flow stream and $D_s$ is the diameter of the flow stream.

Since $C_D$ is a function of droplet properties and flow stream characteristics, $C_D$ is the same for droplets of different radii.

The relaxation time for a droplet with a radius of $a_1$ or $a_2$ are given by:

$$\tau_1 = \frac{\rho_{liquid}4(a_1)^2C_D}{18\mu_{air}} \tag{15}$$

$$\tau_2 = \frac{\rho_{liquid}4(a_2)^2C_D}{18\mu_{air}} \tag{16}$$

While relaxation time gives an indication of the time taken for a droplet to adjust to a new set of forces, Stopping Distance is a measure of how far a droplet will travel until it reaches a new steady state velocity under these forces. For instance, stopping distance S of a droplet traveling at velocity $V_0$ will give the distance the droplet will continue to travel after the applied force has been removed. Stopping distance is particularly important when it comes to determining the likelihood of particle deposition due to inertia. The stopping distance for the situation where the motive force in the direction of travel is removed is given by $$S = V_0\tau \tag{17}$$

where $V_0$ is the initial velocity.

The degree to which droplets will 'stick' to the streamlines, or diverge from them, is characterized by the Stokes number St which is a dimensionless parameter. St is the ratio of droplet stopping distance to some measure of the size of the object causing the flow to diverge:

$$St = \frac{S}{D} = \frac{\tau U_0}{D},\ Re < 1.0 \tag{18}$$

where D is a characteristic length of the obstruction, or flow system (for instance the diameter of a regular obstruction) and Re is the initial particle Reynolds number.

Like Reynolds number, Stokes number is dimensionless. Stokes number can be understood as the 'persistence' of a particle divided by the size of an obstruction. As St approaches zero, particles will follow the streamlines perfectly. As St increases, a particle's resistance to any changes in direction will increase, resulting in increasingly more streamlines being crossed by the particle in regions of rapid flow direction change. If a particle has the same values of Re and St for similar geometric conditions, particle motion will be the same-equality of Re ensures that the flow conditions are similar, while equality of St ensures that particle motion in the flow fields is similar.

Inertial Losses

Inertial losses occur when particles with high inertia are required to follow rapidly changing flow conditions-such as flow around a bend. Recall that a particle's Stokes number provides an indication of whether a particle's inertia is sufficiently small for it to follow the streamlines, or large enough to lead to little or no conformity to the changing flow pattern. Thus, particles with very small St would be expected to have a high penetration efficiency through a convoluted flow system, and particles with a high St would be expected to deposit out of the droplet stream rapidly. For laminar flow, the penetration efficiency around a bend of φ radians may be estimated using the empirical expression:

$$P = 1 - \varphi St \quad (19)$$

where:

$$St = \frac{\tau U_0}{D} \quad (20)$$

$U_0$ is the average flow velocity of the droplets.

The fraction of the number of droplets with radius $a_1$ and $a_2$ staying in the flow stream is given by:

$$P_1 = 1 - \varphi St_1 \quad (21)$$

$$P_2 = 1 - \varphi St_2 \quad (22)$$

Rearranging yields:

$$1 - P_1 = \varphi St_1 \quad (23)$$

$$1 - P_2 = \varphi St_2 \quad (24)$$

Dividing both sides of (23) by (24):

$$\frac{1 - P_1}{1 - P_2} = \frac{\varphi St_1}{\varphi St_2} \quad (25)$$

Since φ represents the angle of deflection of the stream which is the same for both droplets of different radii so that:

$$\frac{1 - P_1}{1 - P_2} = \frac{St_1}{St_2} \quad (26)$$

Since $U_0$ and D from equation (20) is the same for both droplets of different radii reduce (26) to:

$$\frac{1 - P_1}{1 - P_2} = \frac{\tau_1}{\tau_2} \quad (27)$$

Substituting for the relaxation times into equation (27) yields:

$$\frac{1 - P_1}{1 - P_2} = \frac{\tau_1}{\tau_2} = \frac{\frac{\rho_{liquid} 4 (a_1)^2 C_D}{18 \mu_{air}}}{\frac{\rho_{liquid} 4 (a_2)^2 C_D}{18 \mu_{air}}} = \frac{(a_1)^2}{(a_2)^2} = \left(\frac{a_1}{a_2}\right)^2 \quad (28)$$

Setting equation (28) equal to α:

$$\frac{1 - P_1}{1 - P_2} = \left(\frac{a_1}{a_2}\right)^2 = \alpha \quad (29)$$

Normalizing the fraction of the number of droplets with radius $a_1$ and $a_2$ staying in the flow gives:

$$P_1 + P_2 = 1 \quad (30)$$

Rearranging (30):

$$P_1 = 1 - P_2 \quad (31)$$

Rearranging (29):

$$1 - P_1 = \alpha(1 - P_2) \quad (32)$$

Substituting (31) into (32):

$$1 - P_1 = \alpha P_1 \quad (33)$$

Rearranging and substituting back for α:

$$1 = \alpha P_1 + P_1 = (1 + \alpha) P_1 \quad (34)$$

$$P_1 = \frac{1}{1 + \alpha} = \frac{1}{1 + \left(\frac{a_1}{a_2}\right)^2} \quad (35)$$

Calculation of the fraction of the number of droplets with radius $a_1$ and $a_2$ staying in the flow with $a_1$=5 microns or diameter 10 microns and $a_2$=0.5 micron or diameter 1 micron.

$$P_{larger} = \qquad (36)$$

$$P_1 = \frac{1}{1+\alpha} = \frac{1}{1+\left(\frac{a_1}{a_2}\right)^2} = \frac{1}{1+\left(\frac{5}{1}\right)^2} = \frac{1}{1+25} = 0.0099 = 1.0\%$$

Larger droplets with a diameter of 10 microns have a 1.0% chance of staying in the flow stream and a 99.0% chance of depositing onto the redirector.

$$P_{smaller} = \qquad (37)$$

$$P_2 = \frac{1}{1+\alpha} = \frac{1}{1+\left(\frac{a_2}{a_1}\right)^2} = \frac{1}{1+\left(\frac{1}{5}\right)^2} = \frac{1}{1+\frac{1}{25}} = 0.990 = 99.0\%$$

Smaller droplets with a diameter of 1 micron have a 99.0% chance of staying in the flow stream and a 1.0% chance of depositing onto the redirector.

Wet Versus Dry Fogging

The solution content or volume per droplet is given by:

$$V = \frac{1}{6}\pi d^3$$

Comparing the volume of a 1-micron droplet, 10-micron droplet and 20-micron droplet:

$$V(1\ \mu\text{m}) = \frac{1}{6}\pi(1\ \mu\text{m})^3 = 0.5236\ \mu\text{m}^3 = 5.236\times10^{-13}\ \text{ml}$$

A 10-micron droplet yields:

$$V(10\ \mu\text{m}) = \frac{1}{6}\pi(10\ \mu\text{m})^3 = 523.6\ \mu\text{m}^3 = 5.236\times10^{-10}\ \text{ml}$$

$$\frac{V(10\ \mu\text{m})}{V(1\ \mu\text{m})} = \frac{5.236\times10^{-10}\ \text{ml}}{5.236\times10^{-13}\ \text{ml}} = 1000$$

A 20-micron droplet yields:

$$V(20\ \mu\text{m}) = \frac{1}{6}\pi(20\ \mu\text{m})^3 = 4186\ \mu\text{m}^3 = 4.186\times10^{-9}\ \text{ml}$$

$$\frac{V(20\ \mu\text{m})}{V(1\ \mu\text{m})} = \frac{4.186\times10^{-9}\ \text{ml}}{5.236\times10^{-13}\ \text{ml}} = 7994 \cong 8000$$

A 10-micron droplet has 1000 times larger volume of solution than a 1-micron droplet. A 20-micron droplet has 8000 times larger volume of solution than a 1-micron droplet.

The increased amount of liquid in the larger droplets can leave surfaces and items visibly wet. The larger droplet size also prevents penetration of materials and diffusion into remote spaces, both directly, due to their size, and indirectly because their greater mass causes them to move and diffuse slowly while quickly condensing out of the air. The larger droplets can bridge small gaps because of the surface tension of the fluid. The smaller droplets can easily penetrate into the small gaps and cracks to deliver decontaminating solution deep within the small gaps and cracks.

Redirectors

The invention creates collision points using redirectors within the pathway that the fog travels (also referred to as fog flow paths) during the process of exiting the machine so that those collision points can capture the larger particles and remove them from the flow path, thus allowing the smaller particles as the primary product that enters the room. In other embodiments, the redirectors are comprised of corners or angles formed by two joined surfaces or a sharp turn in the air flow pathway.

Multiple methods and embodiments are described as part of the invention for accomplishing this goal.

In one embodiment, the invention addresses the ability to deliver this technology in a mobile unit without requiring a long vertically-oriented tube. Such vertical tubes are known in the art. The tube of the present invention, in one application, is about 2 feet in length, requiring the fog to make contact with collision points via the redirectors as the fog particles pass through the 2-foot tube. These collisions collect larger particles and allow them to drain back down into an atomization chamber of the fog-producing device. This results in particles exiting the end of the tube that are smaller in size than they would be without the collision points/redirectors. As explained further below in conjunction with FIGS. 20A and 20B, the smaller fog particles may not strike a redirector due to the pressure gradients near the redirector surfaces. The redirectors are present with the intent that the larger particles strike a redirector and the smaller particles continue along the flow path without striking a redirector. Essentially, once a particle strikes a redirector, it is out of the flow path.

In lieu of adding a tube to the exit port of a fog producing device, another embodiment, as further described below, accomplishes the goal of capturing larger fog particles and allowing the smaller particles to reach the target to be treated, by modifying tubes that are internal to the fogger mechanism. This modification creates similar collision points via redirectors immediately after the particles are created by the transducers in an atomization chamber of the fog-producing device. Again, this causes larger particles to be blocked as they follow the fog flow paths and they drain back down into the atomization chamber. This results in particles exiting the atomization chamber that are smaller in size than they would be without the invention.

Additional techniques are considered, recognizing that the "tube" referred to herein can reasonably comprise any pathway the fog travels through after generation and before entering the room or reaching the surface or target to be treated.

The inventive criterion for this fog pathway is that the fog collides with collision surfaces provided by redirectors, surface corners, or any angled surface. Although the various Figures depict redirectors set at about a 45-degree angle relative to the fog flow path, a wide range of angles is suitable for achieving the beneficial results of the invention, i.e., fog particles to strike or pass proximate redirector surfaces to change or redirect the angle at which the fog travels. After colliding with one or more of these surfaces, the fog continues along the fog pathway. That is, the smaller fog particles continue along the fog pathway, but the larger fog particles fall from the fog pathway. Multiple different fog pathways and redirector designs are described, such as those illustrated in the Figures.

Another example of an enclosure that includes redirectors is a wall enclosure where the fog travels through pathways in the wall in order to enter the room or space being treated. The pathways are defined by redirectors that serve as collision points and accomplish the objective of preventing larger particles from exiting the fog-producing machine, while allowing the smaller particles to exit the fog-producing machine and enter the room being treated.

This same concept of using redirectors as collision points can be applied to many different form factors, including portable boxes, portable "thermos" type devices, single operator carts, fixed permanently mounted units etc.

Essentially, the invention relates to redirecting the fog so that it collides with engineered surfaces to accomplish the goals of the invention.

Thus, the invention describes collision points via redirectors that are effective when fog passes through a pathway in route to exiting the machine or an enclosure and entering a room or space to treat the room or space.

A fogger is any device that creates a fog, typically comprising a cloud of water droplets and in the context of this invention the water droplets include another substance, in particle, vapor, or aerosol form, that performs a beneficial function, such as those functions described below.

The ultrasonic fogger/nebulizer is a common design for fog generation, has few moving parts, minimal power requirements, does not require special temperature or pressure conditions and is easy to install and use. This simplicity makes its use advantageous for a wide variety of applications and this type of fog generation is the primary generation method to which the teachings of the invention can be applied.

However, the present invention can be applied to any fog generation method or device as a tool for reducing the size of the vapor particles that are released by a fogger into the environment. The basic requirements for use with the present invention are that the fogging method produces at least some particles of the desired size, which are less than about 2.5 microns, and that those particles pass through the present invention's collision points of redirectors within the pathway before entering the environment for treating purposes.

An ultrasonic fogger/nebulizer uses water soluble mediums (or liquid of similar consistency) to produce fog. The fogger uses transducers that have a resonant frequency typically ranging from 1600 to 2600 kHz. They create ultrasonic waves which are focused on water and the high-energy vibrations cause the water to turn into a fog-like atomized cloud, thus generating fog. This process produces fog that consists of sub-micron-sized particles up to about 20-micron in diameter. The fog is generated in an atomization chamber where air is brought in by a low-pressure fan causing the fog to be driven out of the chamber via the pathway and across collision points via redirectors as described herein. The fog emitted after passing through the inventive pathways could be described as a dry-feeling aerosol vapor.

This principle of fog formation can be used in many applications. Add insecticides to water in the fogger and its fog can be used to kill insects; add nutrient solutions to water and the fog provides a nutrient treatment to plants; add a disinfectant to the water and it will disinfect, etc.

As described at length herein, it is important in many intended applications that the fog particle size is small enough to infiltrate deep within fabrics, porous surfaces and cracks within otherwise smooth surfaces. The presence of large particles in these applications can hinder this objective by covering smaller openings and cracks and thus impeding the ability of active ingredients to reach their treatment target.

In other applications, it is important to avoid the creation of condensation or even precipitation of the fogged fluid, which could damage electronics, sensitive materials, products in the environment or create the need for cleanup associated with the wetness deposited in the treated area.

The described invention limits the size of the particles that exit the fogger or exit a fog pathway (e.g., an enclosed volume, a tube, or a wall) before entering a room or region to be treated. Their small size allows the particles produced to diffuse evenly throughout the treated space in a gas or smoke-like fashion. Their small size allows the product being fogged to treat extremely small cracks, crevices and hidden away spaces. And the small size of these particles minimizes the possibility of leaving condensation on surfaces that would create a wet feel and possibly damage the contents of the treated space.

Experimental data shows that emission (from the fogger) of the smallest size particles was significantly increased by use of the invention, while the emission of larger particles was decreased. After 30 minutes of the fogging machine operating with the invention, 98% of the total count of particles were less than 2.5 μm per $cm^3$. These smaller particles disperse more evenly through the air column and are able to come in contact with smaller spaces, cracks and crevices on surfaces and within fabrics.

Experimental data also shows that after 30 minutes of a fogging operation, the dew point in a room without a fogger constructed according to the teachings of the present invention, was 65° F. With the inclusion of the invention, the dew point in the room under the same operating conditions was 40° F. Condensation is easily formed at 65° F. and will not form under normal operating conditions at 40° F.

Experimental data also shows that with the use of a prior art fogger, the relative humidity in a room, after 30 minutes of fogging, caused a relative humidity in the room of between 85-95%. Use of the same fogging machine according to the teachings of the invention, the relative humidity in the room under the same operating conditions was 35%. Condensation is easily formed at 85-95% relative humidity and will not under normal operating conditions form at 35% relative humidity.

Over the course of collecting the data, the test room was always dry to the touch after utilizing the invention and extremely wet when using a prior art fogging device.

The invention is described below in conjunction with each of the figures.

FIG. 1 illustrates a simplistic standard sonic fogger arrangement shown to assist in describing the invention.

The invention does not specifically require the use of a sonic fog generating device, but this is a common technique for generating small fog droplets and is the generation technique utilized to describe the application and advantages of the invention.

However, the invention can be applied to any other fog-generating techniques, such as thermal or mechanical fog generation techniques that produce similar results.

The relevant elements of FIG. 1 for the purpose of exhibiting the invention are:

i. Airflow provided by a low-pressure fan 101
ii. Atomization chamber 102
iii. Sonic transducer 103
iv. Fog exit tube 104

The teachings of the present invention are employed after the fog has been created and is exposed to a low-pressure fan which generates airflow 101 and sends the fog on its path to the area being treated via the exit tube 104, which channels the fog as it leaves the atomization chamber 102

Fog droplets generated in the atomization chamber and joining the airflow pathway are a variety of sizes, ranging from sub-micron to 50 microns, depending upon the specific functionality and design of the fogger's generation process.

The invention affects these fog droplets in a manner that increases the number of sub-micron particles introduced to the treated space and decreases the number of larger ones.

While an accurate count or distribution of particle sizes exiting the fog pathways with redirectors cannot be determined, generally, the majority of the exiting particles are between about a sub-micron size up to about 2.5 microns. As known by those skilled in the art, it is not possible to remove all over-sized particles from the fog that exits a redirector assembly. However, it has been determined that about 98% of the output fog particles are less than about 2.5 microns in size and about 79% are less than about 1 micron in size. Notwithstanding the inability to determine an accurate particle size count, clearly the inventive fog flow paths with redirectors reduces the average particle size that is introduced into the room or material to be treated.

The following Figures illustrate multiple air flow pathway styles and integration of the invention into those pathway styles at various locations along the fog pathway.

It is desired that each of these pathway tubes or other pathway structures are manufactured utilizing plastic molding production methods, requiring only the assembly of various parts after production.

Figure 2:
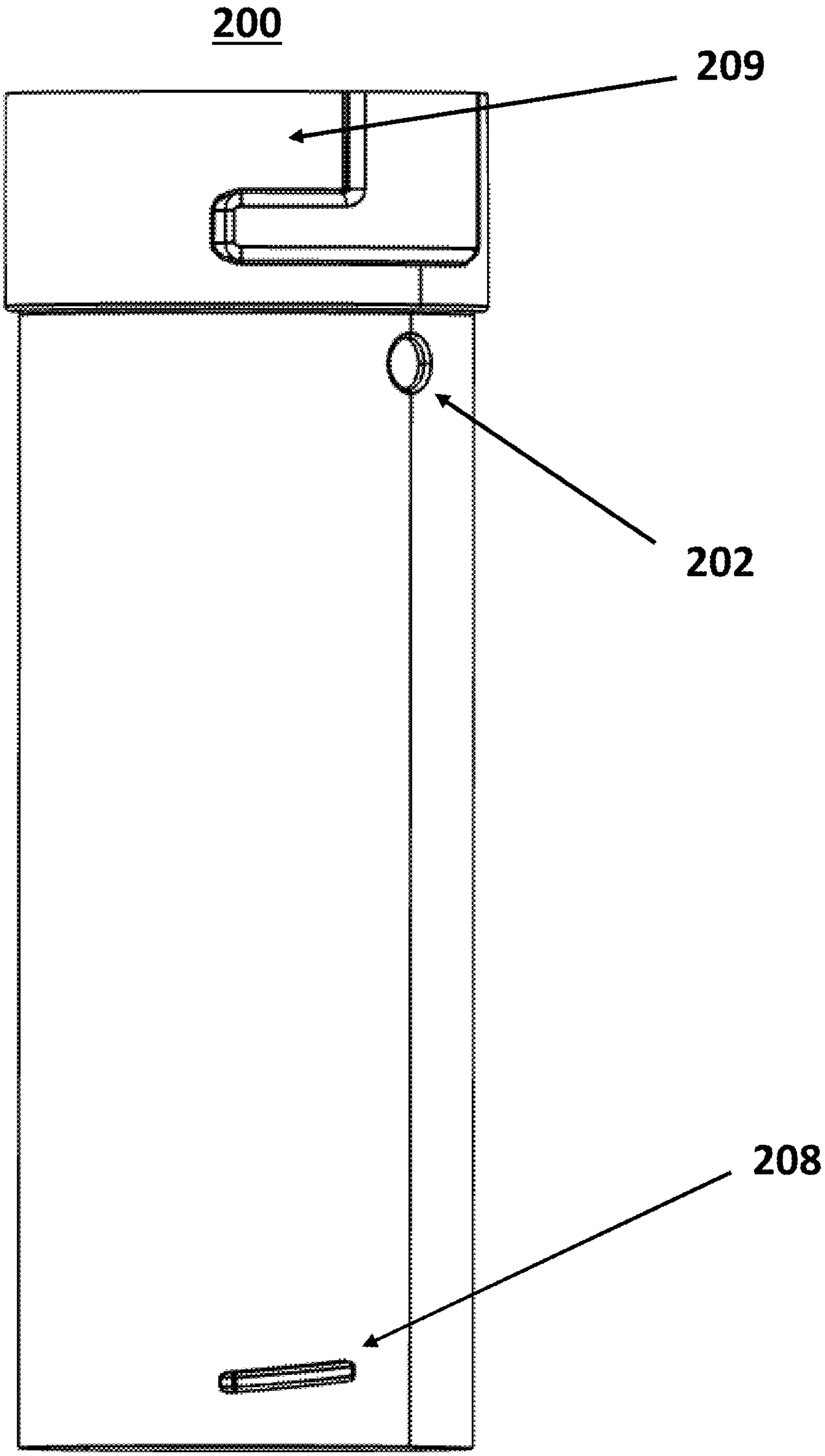
FIG. 2 depicts a tube or pathway which in conjunction with the inventive redirectors embodies the teachings of the present invention, for use with a fogger, such as the fogger of FIG. 1.

FIG. 2 illustrates a 10-inch tube 200.

The tube exemplifies a structure for defining a fog pathway for the capture of over-sized particles according to the teachings of the present invention. The tube 200 is disposed at a terminal end of the fog exit tube 104 of FIG. 1, that is, the tube 200 is external to the fog-producing device.

In one embodiment, the tube is 10-inches long having a male end 208 and a female end 209 so that two or more tubes can be joined together to create a single long pathway.

In one embodiment the tube 200 has a 3" diameter, is 10" long and is sized to distribute fog produced by a 4-transducer sonic fogging unit. The tube 200 can be increased or decreased in length and diameter to accommodate specific dimensions and configurations of a fogger that it is mated with and also to accommodate the amount of fog being produced and the required air flow rate for the treatment application.

Figure 3:
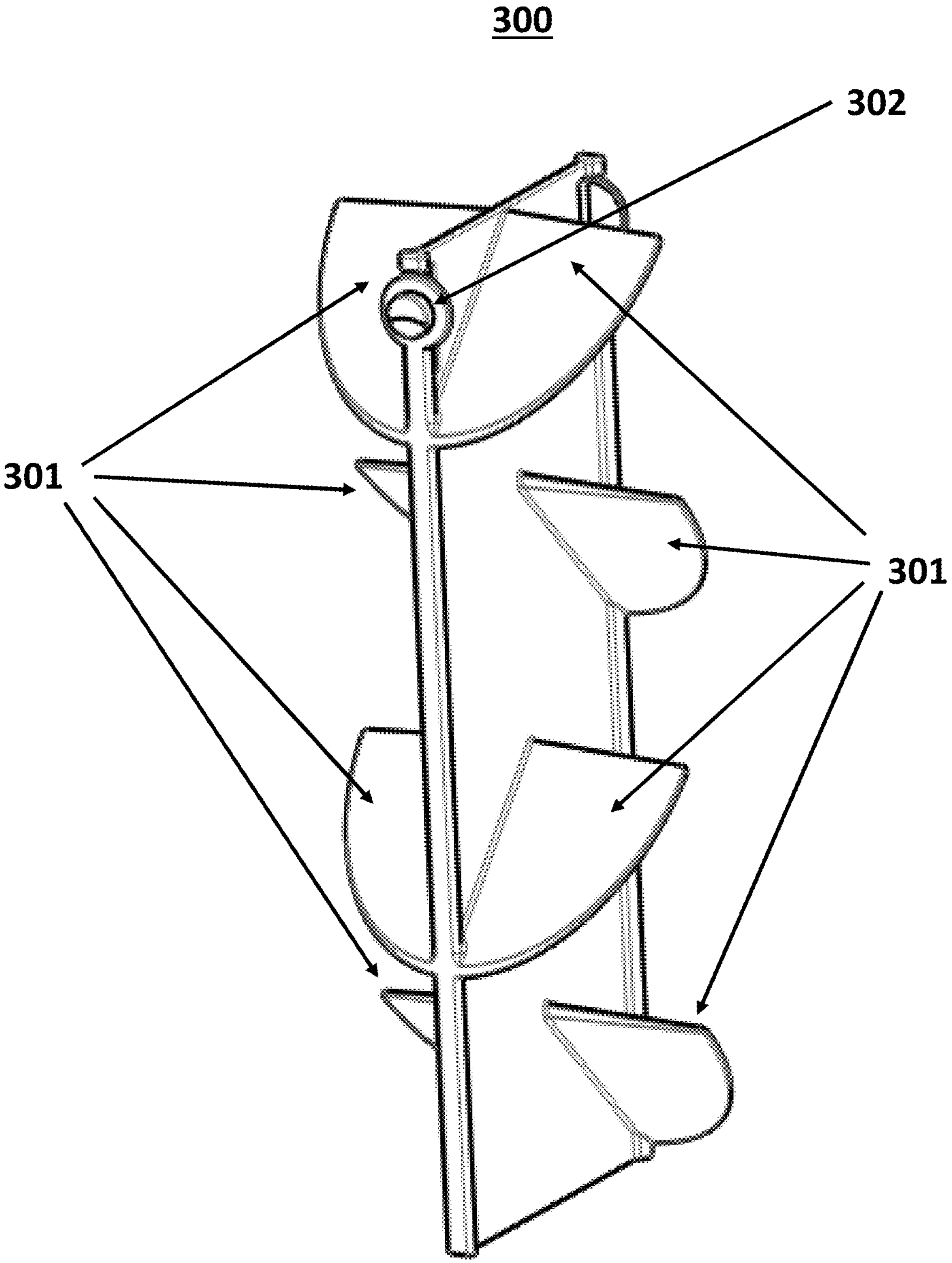
FIGS. 3 and 4 depict two different designs of fog redirector of the present invention.

FIG. 3 illustrates a 10-inch redirector insert 300 for the tube 200.

This insert embodies the invention as disposed within tube 200. The insert 300 has redirectors 301 along the fog pathway as the fog moves through tube 200 and thereby through the redirector insert 300. As can be seen, the redirectors 300 are attached to both surfaces of a substrate.

The insert 300 (and its attached redirectors 301) is inserted into the tube 200 and is secured in place by tabs 302 that lock into place at mating elements 202 of the tube 200. See FIG. 2.

Once inserted and locked in place the insert 300 becomes an integral part of the tube 200, resulting in an assembled working embodiment of the present invention.

As the fog travels through the fog droplet airflow path through tube 200, the fog is redirected along its route by collisions with the redirectors 301. The larger fog droplets are more likely to collide with the redirectors 301 (than the smaller fog particles) as they travel along the airflow path. Once the larger particles collide with a redirector, they are eliminated from the air flow stream, collect on the redirector and tube surfaces and as they build in volume, will eventually drain down the tube 200 back into the atomization chamber. It is less probable that smaller droplets will collide with the redirectors 301. These smaller droplets are therefore able to exit the fog droplet flow path channel for delivery to the treated space.

In one embodiment, the insert 300 has a diameter and length designed for insertion into the tube 200. The insert can, of course, be increased or decreased in length or diameter for use with smaller or larger fogger tubes. Note that the free edge of each redirectors is shaped to fit within the tube, i.e., that shape is complementary to the shape of the inside surface of the tube 200.

Figure 4:
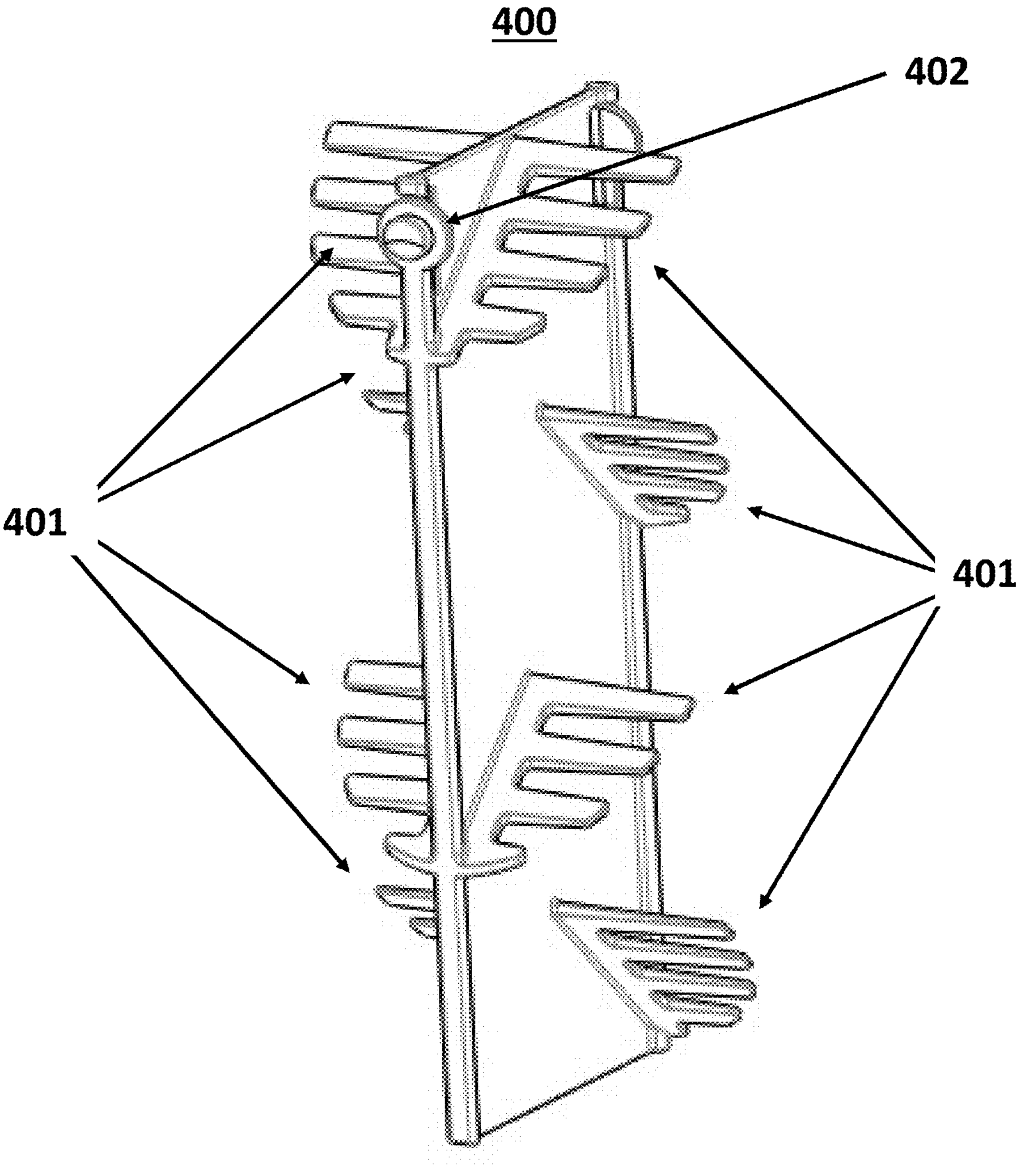

FIG. 4 illustrates another redirector insert style (referred to as comb style redirectors) that may be employed in a fogger outlet tube, such as the 10-inch tube 200 of FIG. 2.

In the FIG. 4 embodiment an insert 400 locates redirectors 401 along the pathway the fog travels as it moves through an enclosed surface or tube, such as the tube 200.

The insert 400 is inserted into tube 200 and is secured by tabs 402 which lock into place with the mating elements 202 of the tube 200 of FIG. 2.

This style of the redirectors 401 provides a slightly higher volume of fog production, while being less efficient at ensuring larger particles are eliminated from the fog droplet path airflow due to the comb-like structure of each redirector.

Figure 5A:
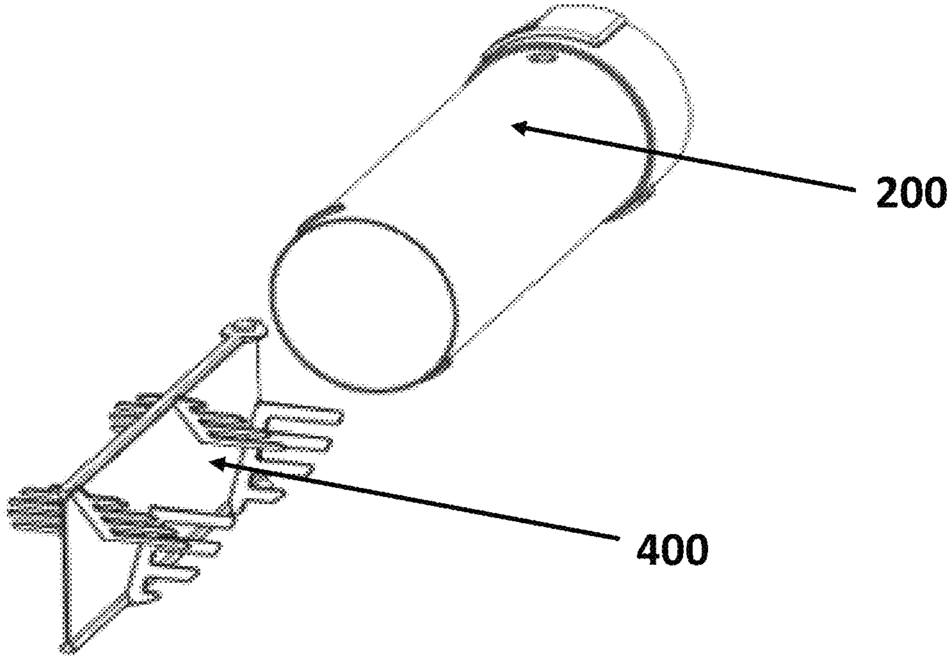
FIGS. 5A and 5B depict a tube and redirectors within the tube according to the present invention.
Figure 5B:
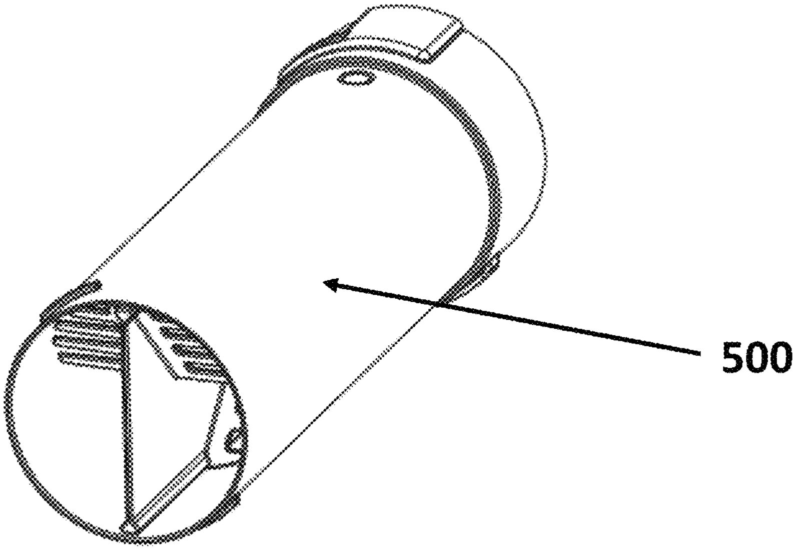

FIGS. 5A and 5B illustrate insertion of an insert (substrate) with redirectors into a 10-inch tube to create a completed 10-inch tube redirector assembly.

In this example, redirector insert 400 (FIG. 4) is inserted into tube 200 (FIG. 2) to form a completed 10-inch tube assembly 500.

Figures 6A, 6B:
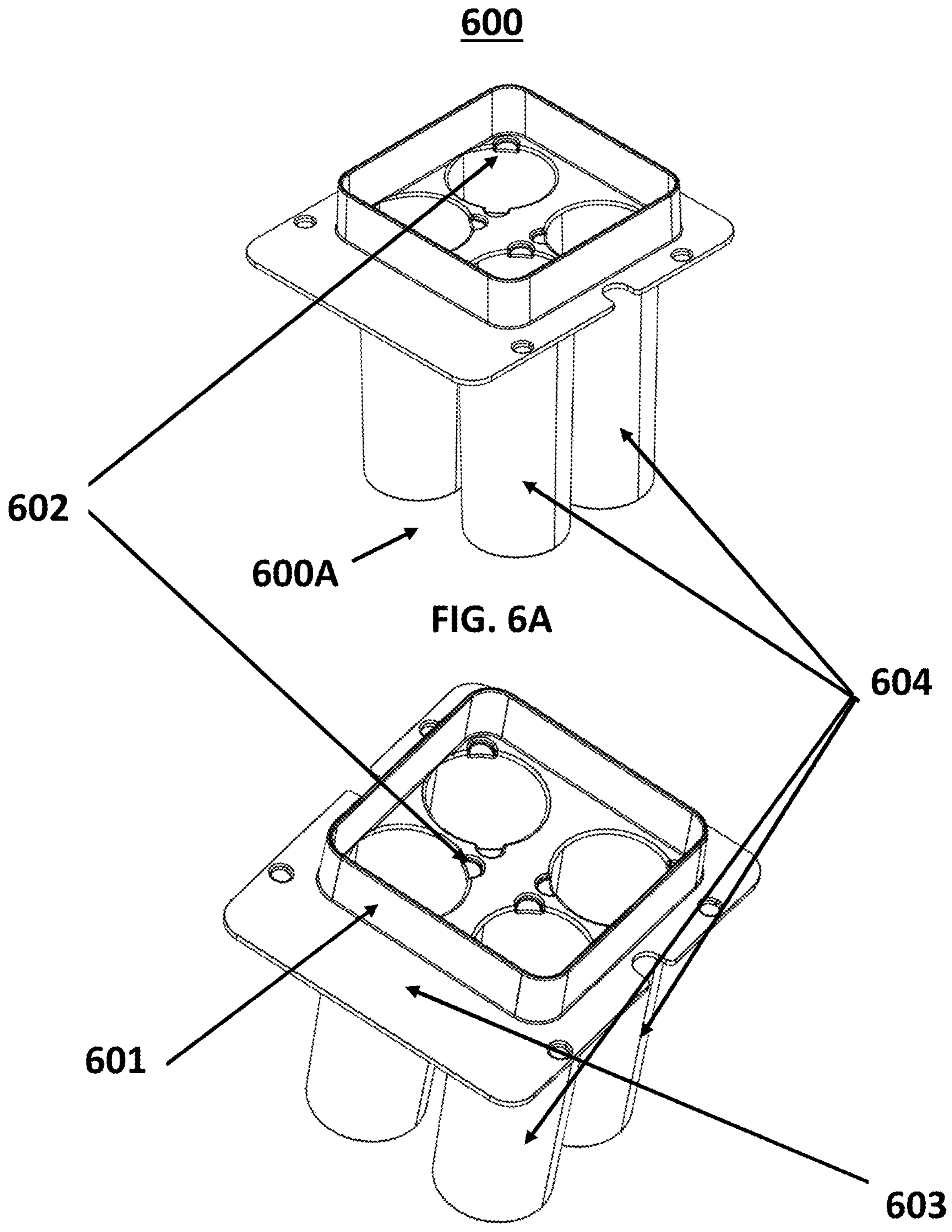
FIGS. 6A and 6B depict a four-tube assembly in two separate images at slightly different angles.

FIGS. 6A and 6B illustrates a four-tube assembly 600 in two separate images at slightly different angles.

The assembly 600 is employed in a fogger with four (4) sonic transducers, thus requiring four exit tubes 604. The assembly 600 is mounted atop a 4-transducer fogger unit. This arrangement thus provides four tubes 604 each situated over an individual transducer. Placement of the tubes 604 integrates the redirectors into the pathway as the fog droplets travel up the tubes 604.

In this embodiment the redirectors within the four tubes are engaged immediately as the fog droplets exit the atomization chamber 102 of FIG. 1. Thus element 104 in FIG. 1 is replaced by the four-tube assembly 600, thereby placing the tubes 604 and the redirectors within the tubes immediately above the transducers where the fog is generated. This converts the fogger with the tube 104 into a fogger of the present invention.

This embodiment with four transducers and thus four tubes, each tube enclosing a plurality of redirectors, allows the use of a shorter length of external tubing, by starting the redirecting action as the fog begins to exit the chamber.

Generally, the tubes 604 are similar, if not identical to the tube 104 of FIG. 1 absent the inclusion of redirectors within the tubes 604.

This location places a lower end of each tube at the fogger manufacturer's prescribed distance from the high-water level of a reservoir 105 and appropriately aligned over each of four sonic transducers. Note that only one sonic transducer 103 is shown in FIG. 1.

In another embodiment, assembly 600 can be used with a single sonic transducer unit, or in another embodiment the assembly 600 is modified to include more than four tubes that are aligned with 8, 12, 16 or more sonic transducers.

Figure 7A:
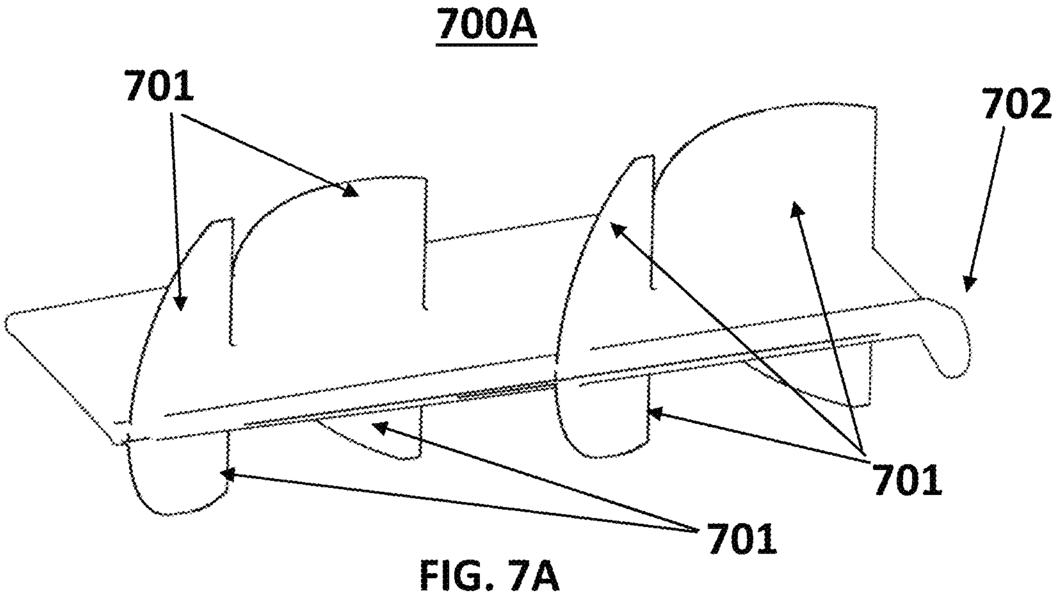
FIGS. 7A and 7B depict different redirector configurations designed for the four-tube assembly of FIGS. 6A and 6B.
Figure 7B:
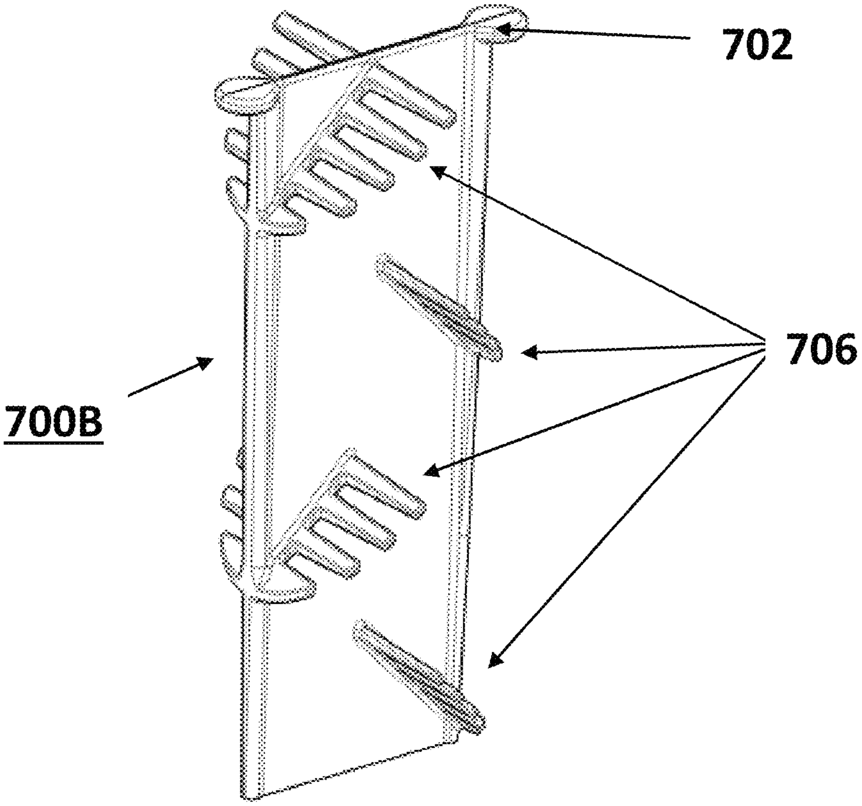

Each of the tubes 604 (FIGS. 6A and 6B) has an insert 700A (see FIG. 7A) with solid style redirectors 701 or an insert 700B with comb style redirectors 706. (see FIG. 7B)

The redirectors 700A and 700B function in the same manner as the redirectors described in FIGS. 3 and 4 but are sized appropriately to be inserted into the smaller tube 604 as positioned above the transducers.

The choice of which redirector style to use (solid or comb-like) is determined by the desired particle count and desired output particle size. Solid-style redirectors 701 reduces the count median diameter particle size introduced into the environment, ensuring that small particles are not overwhelmed by the larger ones and are available to perform their designated task. Utilizing comb style redirectors 706 allows for slightly higher volume fog production but is less efficient at ensuring larger particles are eliminated from the fog droplet path airflow as they travel through the invention The redirector inserts 700A and 700B are set within any one of the tubes described herein with the insert tabs 702 disposed within receiving grooves 602. (see FIGS. 6A and 6B).

Figure 8A:
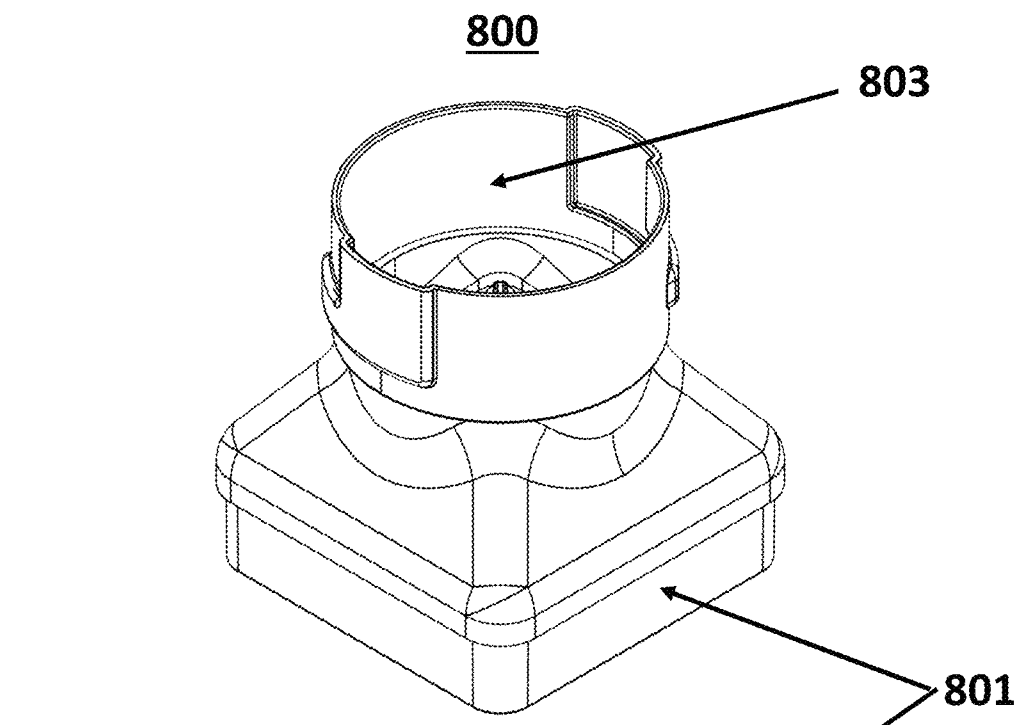
FIGS. 8A and 8B depict two views of a transition piece according to the invention for use with a four-tube assembly of FIGS. 6A and 6B.
Figure 8B:
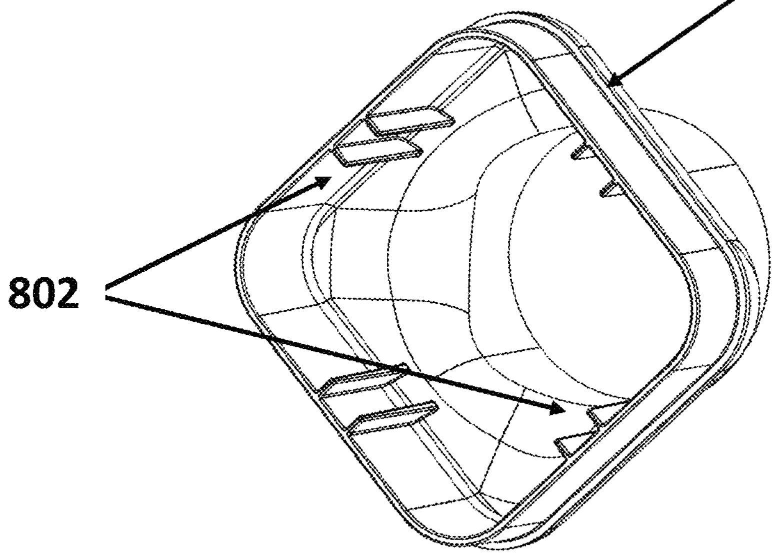

The tube-insert tabs 702 (see FIG. 7) are secured within the receiving grooves 602 when the transition piece 800 (see FIGS. 8A and 8B) is attached to the assembly 600. The insert tabs 702 are secured by tabs 802 built into the transition piece 800 when attached to the assembly 600. The tabs are secured when surface 801 slides onto raised surface 601 (see FIG. 6B) such that the transition piece 800 sets atop the assembly 600 and thereby above the four tubes 604.

The inventive features in the consolidated and smaller tubes of FIGS. 6A and 6B are the same as the inserted redirectors features in the previously described 10-inch tube assembly 500 of FIG. 5.

This transition piece 800 (see FIGS. 8A and 8B) consolidates the fog traveling up the four individual tubes 604 into a single stream up the airflow pathway 803.

In certain applications, it may be necessary to attach a tube with the inventive redirectors to the transition piece 800. The length of this tube and the number of redirectors within it are dependent on the application and the volume of fog required to treat the area or object.

The intent of the four-tube assembly of FIGS. 6A and 6B is to provide the desired number of redirectors (path length) in four tubes in lieu of a single long tube, which may not be feasible in some applications. The wide variety of tube lengths, number of tubes, number of redirectors, and redirector styles allow for use of unique assemblies dependent on the details of the intended application.

Figure 9A:
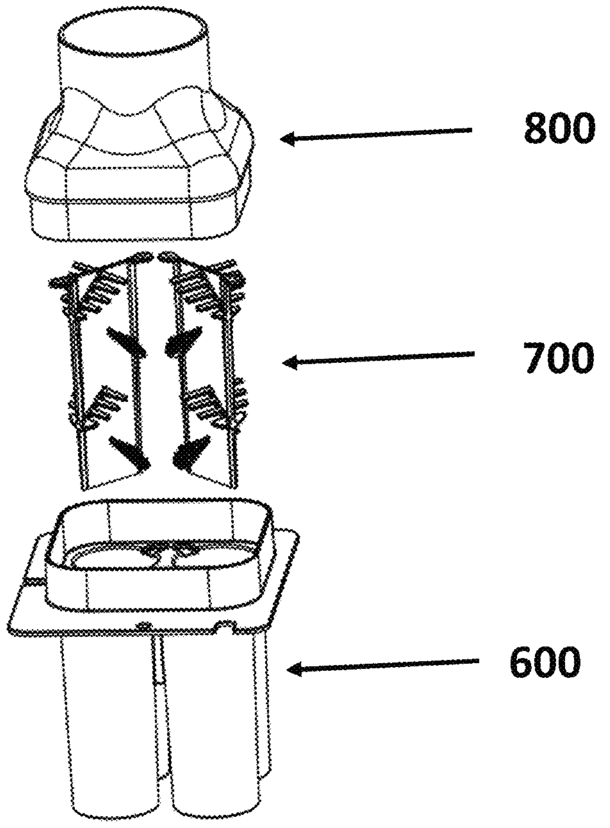
FIGS. 9A and 9B depict two views of the assembly of FIGS. 6A and 6B, the redirectors of FIGS. 7A and 7B, and the transition piece of FIGS. 8A and 8B.

FIG. 9A illustrates an exploded view of the four tubes 600, a set of four tubes inserts 700 (note: there are only two of four required shown in FIG. 9A due to space restrictions) and the transition piece 800.

Figure 9B:
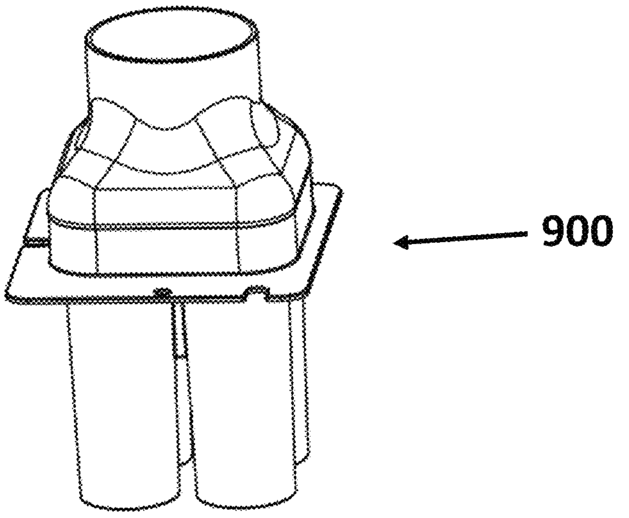

FIG. 9B illustrates the completed assembly 900.

Figure 10:
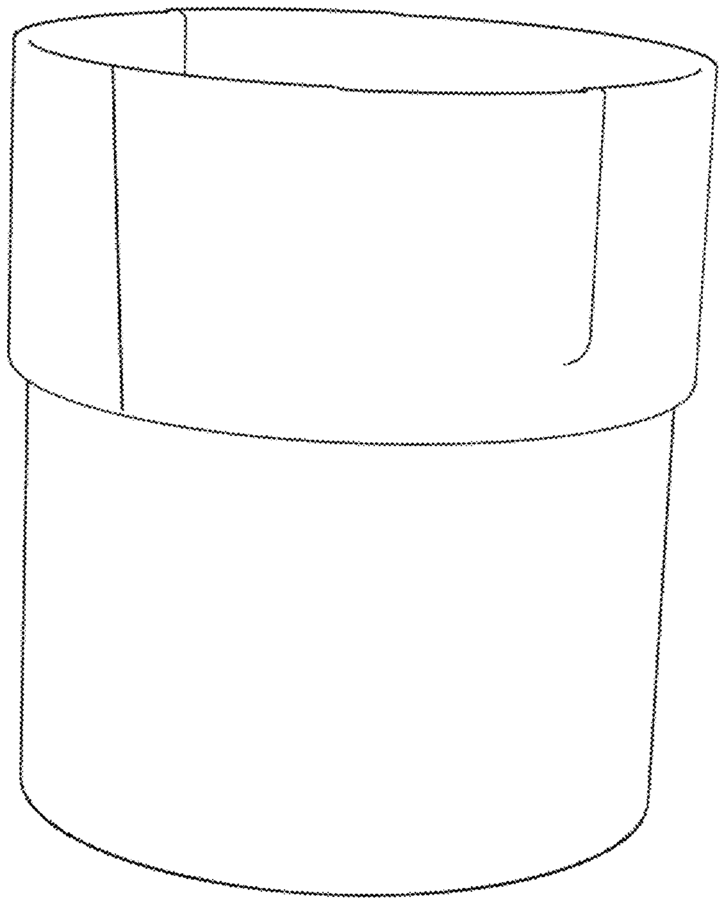
FIG. 10 depicts a coupler for use with the tubes of the present invention.
Figure 12:
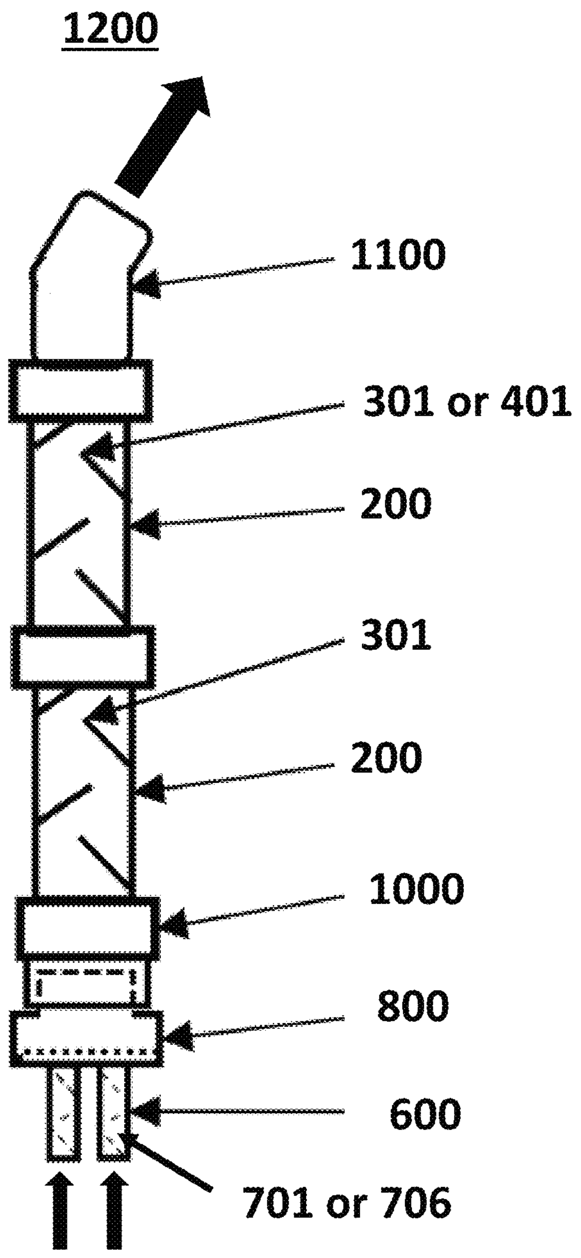
FIG. 12 depicts a completed tube assembly with fog particle redirectors within the tube assembly.

FIG. 10 illustrates a coupler 1000 for creating a junction between the transition piece 800 and the tube 200 so that a complete assembly 1200 of FIG. 12 can pass through a bulkhead for applications when the fogger operates from inside an enclosure, separating it from the treated space.

Beyond coupling piece parts, the coupler 1000 has no effect on the performance of the described inventive features.

Figure 11:
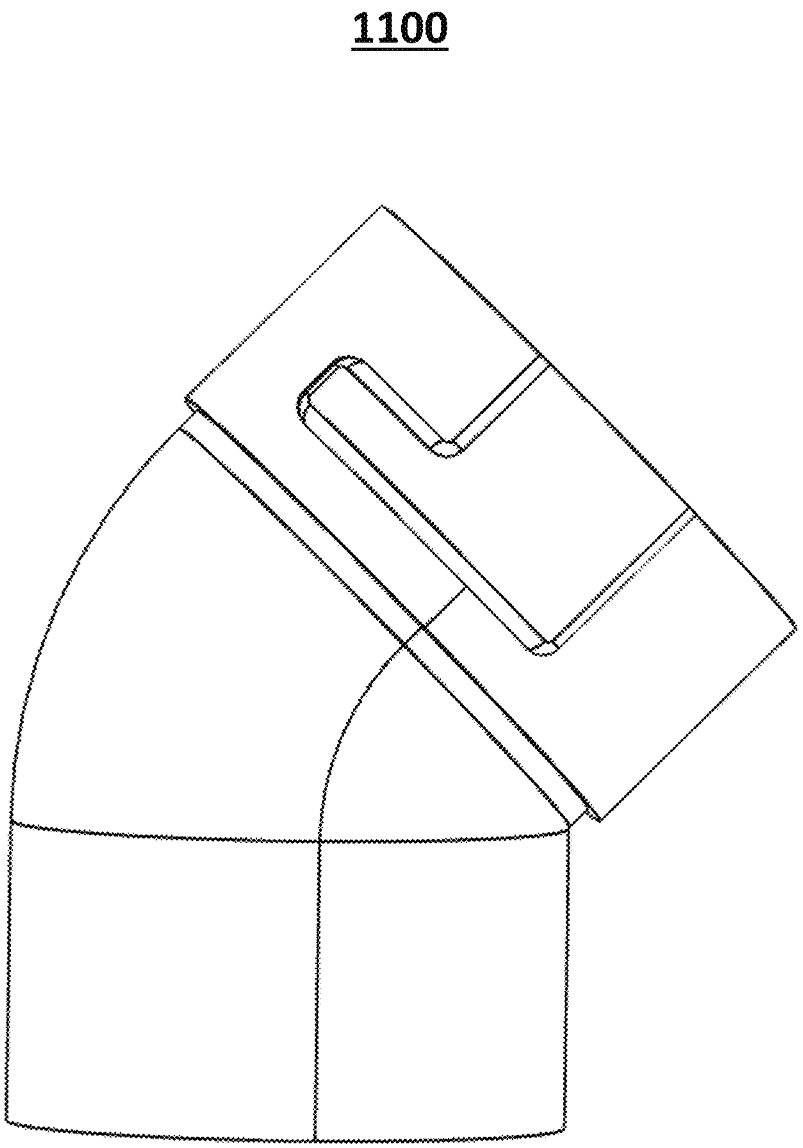
FIG. 11 depicts a swivel piece for use with the tubes of the present invention.

FIG. 11 illustrates a 45-degree swivel tube 1100 that can be inserted into the female end 209 of the uppermost end of the 10-inch tube piece 200, creating the full assembly 1200 of FIG. 12. The sole purpose of the swivel tube 1100 is to allow the end-user to direct fog in a particular direction with options to swivel through 360-degrees. This swivel feature provides one final redirector effect on the particles as they exit the machine. FIG. 12 shows the full assembly 1200 comprising previously discussed components. Fog particles of a wide variety of sizes (sub-micron to 50 micron) enter the bottom of the assembly 1200 pushing upward through the four tubes 600 (only two visible in this figure) where droplets are first affected by redirectors 701 or 706 (see FIGS. 7A and 7B) within the tubes 600 as they move toward and through, the transition piece 800, and the coupler 1000, then into the 10-inch tubes 200 that repeatedly alter the flow direction and eliminate larger fog droplets as the fog moves past the redirectors 301 (see FIG. 3) or the redirectors 401 (see FIG. 4), within the tubes 200. The fog exits the assembly via the 45-degree swivel 1100 and enters the room or space for treatment by the fog.

More or fewer tubes and redirectors may be employed to segregate the fog particles depending on the application, with only the smaller particles (less than about 2.5 microns) exiting the fogger into the area or surfaces to be treated. Generally, more redirectors provide smaller fog particles on average and less overall fog volume.

Larger fog droplets are likely to collide with the redirectors as they travel the fog flow path. Once they collide, the larger particles are eliminated from the air flow, collect on the redirector and tube surfaces, and as they build in volume, will eventually drain down the assembly 1200 back into the atomization chamber. It is less probable that smaller droplets will collide with the redirectors. These smaller droplets are therefore able to exit the fog flow path for delivery to the treated space.

Testing by the inventor and a third party has shown that 98% of the particles which exit the invention assembly 1200 are smaller than 2.5 microns in size. And 79% are smaller than 1.0 microns while 50% are smaller than 0.5 microns when utilizing this invention.

FIGS. 13 through 18B each display an additional application of the invention where the redirectors are disposed in a wall.

This type of redirector arrangement is utilized on equipment where a tube extension for use with the fogger is undesirable. By utilizing a wall as the fog flow path as it exits the atomization chamber in route to the space being treated, the invention can be deployed in a more compact form factor.

In this embodiment, single or multiple walls of the fogger enclosure (box) can be integrated to provide the functionality of the invention. As fog exits the atomization chamber the air flow path directs the fog into a bottom surface of the wall and the fog travels up the wall, through the redirectors, until it exits the top of the wall into the space being treated.

The width, depth and height of each wall section and their resulting fog droplet flow path channels can be scaled to accommodate the required air flow volume of a fogger utilizing the components of the invention.

Figure 13:
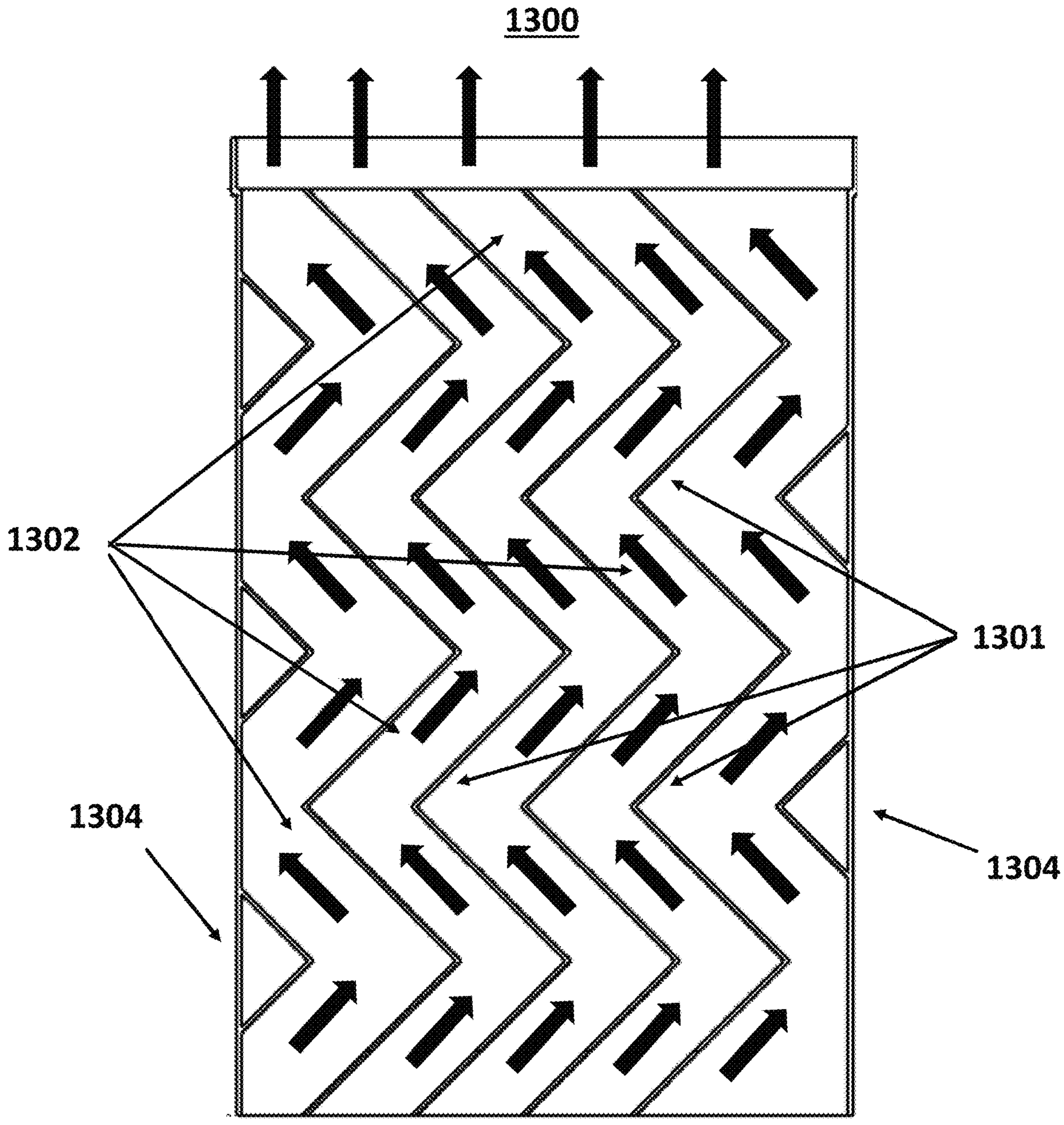
FIGS. 13 and 14 depict alternative embodiments of redirectors mounted to the interior surface of a wall panel.

FIG. 13 illustrates a wall 1300 with multiple continuous fog droplet flow path channels 1302 (formed by parallel redirectors) through which the fog travels. The fog exits the fog-producing system and enters the wall channels 1302 along a bottom surface and flows up the wall. Along this path the fog encounters a redirector at each turn 1301, according to the inventive features. Although the flow paths are depicted as parallel and defined by a zig zag shape, other shapes are considered within the scope of the present invention. The redirecting surfaces, i.e., the wall channels 1302, must be placed and of sufficient number to serve as particle collision surfaces to achieve the objectives of the present invention.

Larger fog droplets are likely to collide with the redirectors as they travel the fog droplet path airflow through the wall with redirectors disposed thereon. Once the larger particles collide with a redirector, the particles are eliminated from the air flow, collect on the redirector and tube surfaces, and as the droplets build in volume, they eventually drain down the wall 1300 back into the atomization chamber.

It is less probable that smaller droplets will collide with the redirectors. These smaller droplets are therefore able to exit the fog droplet flow path channels and be delivered to the treated space.

Figure 14:
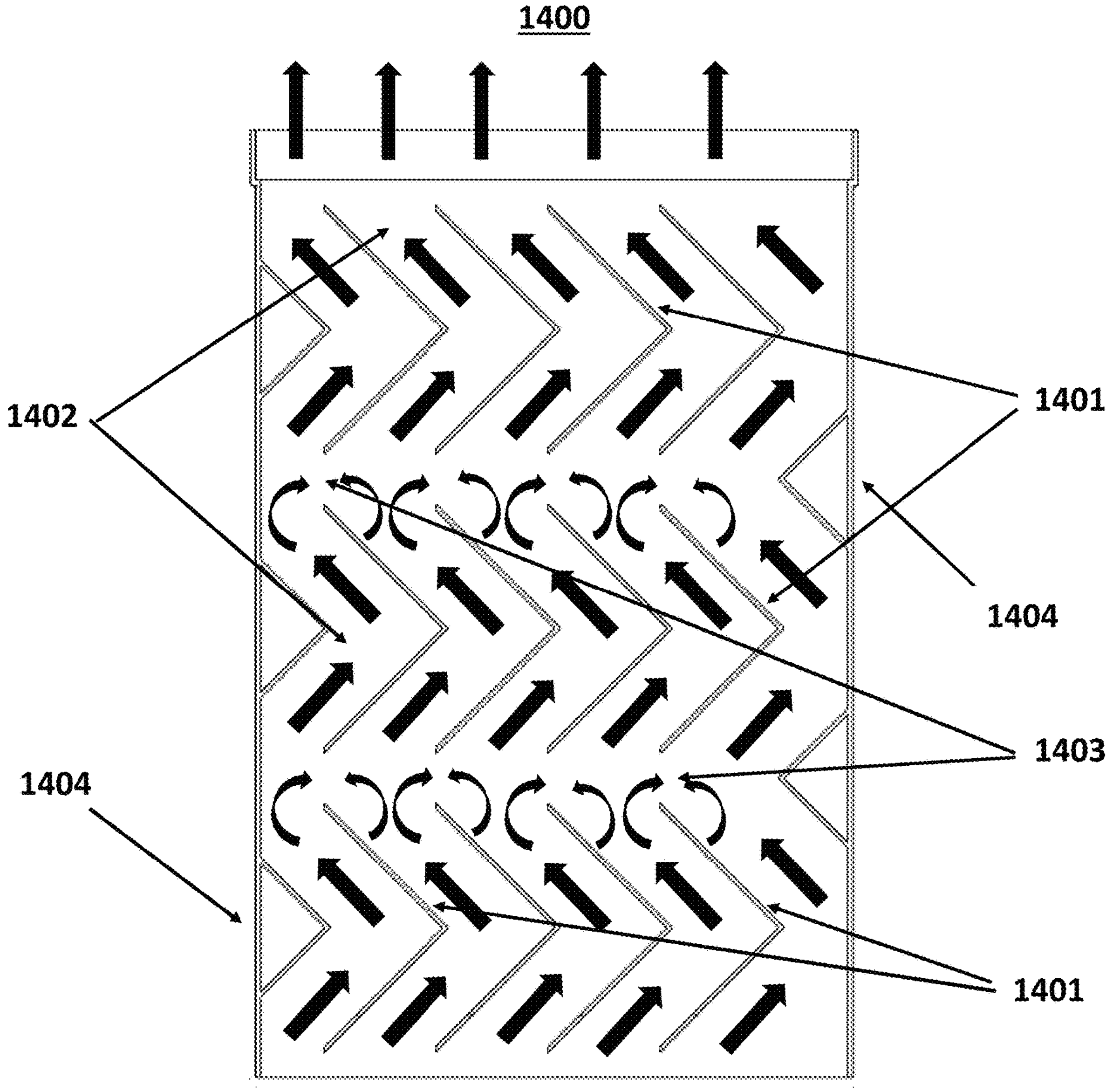

FIG. 14 illustrates this same concept as 1300 (see FIG. 13) with wall 1400, but with non-continuous fog droplet flow path channels 1402 where the fog is influenced by redirectors 1401 so that the flow paths of each flow channel mix 1403 as they travel up the wall.

The redirector 1401 allows for a slightly higher volume of fog production, while being less efficient at ensuring larger particles are eliminated as they travel the fog droplet airflow path from the bottom to the top of the wall.

Figure 15:
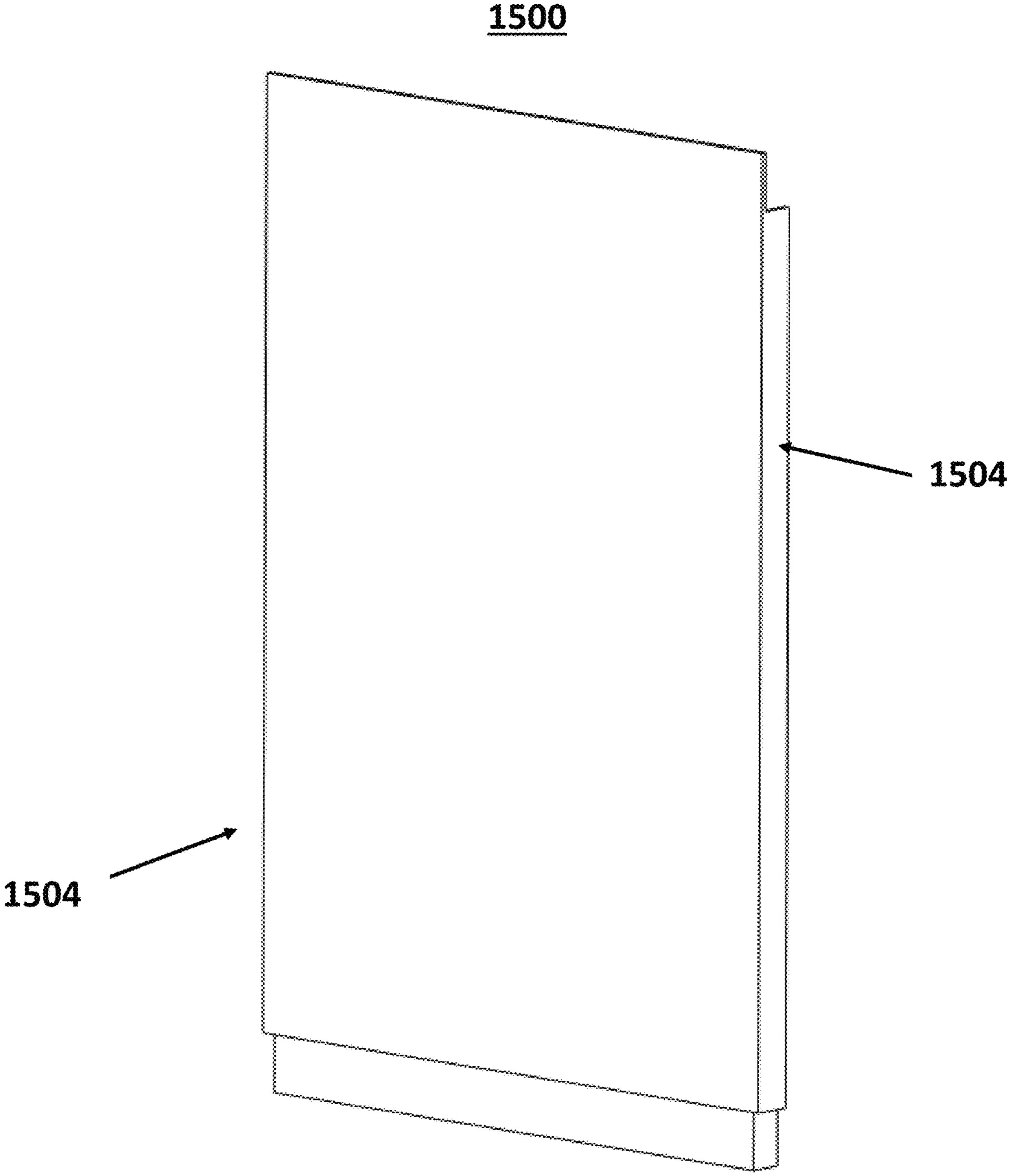
FIG. 15 depicts a wall panel designed to attach to either the FIG. 13 or FIG. 14 wall panels to enclose the redirectors and form the fog flow paths.

FIG. 15 illustrates a front wall surface 1500 that was omitted from FIGS. 13 and 14 to reveal the fog flow paths in the wall. In one embodiment, the front wall surface 1500 and the wall surfaces illustrated in FIGS. 13 and 14 may be manufactured in a plastic molding process requiring that the side of the wall be attached after molding to enclose the fog flow path channels and enable the invention to perform as intended. The front wall surface 1504 snaps into place at location 1304 (see FIG. 13) or location 1404 (see FIG. 14) with clips provided to hold the front wall surface in place, thus completing the wall assembly and completing the fog flow path channels 1302 (FIG. 13) or 1402 (FIG. 14).

Figure 16A:
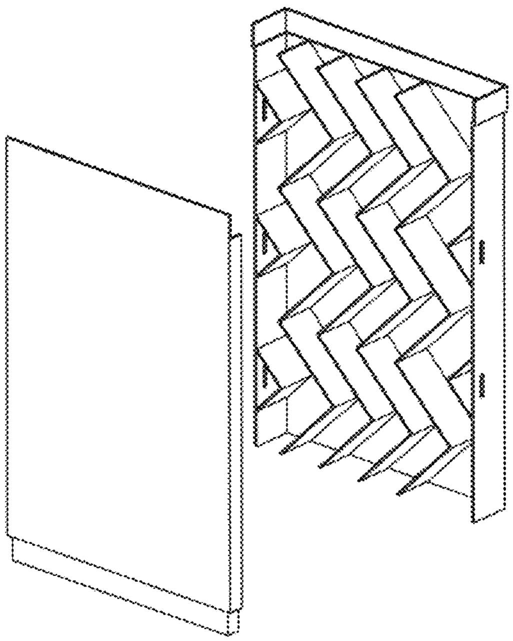
FIGS. 16A, 16B, 17A, 17B depict the wall surfaces of FIG. 13 and FIG. 14 with the wall surface of FIG. 15 attached completing the wall with redirectors embedded in the assembly.
Figure 16B:
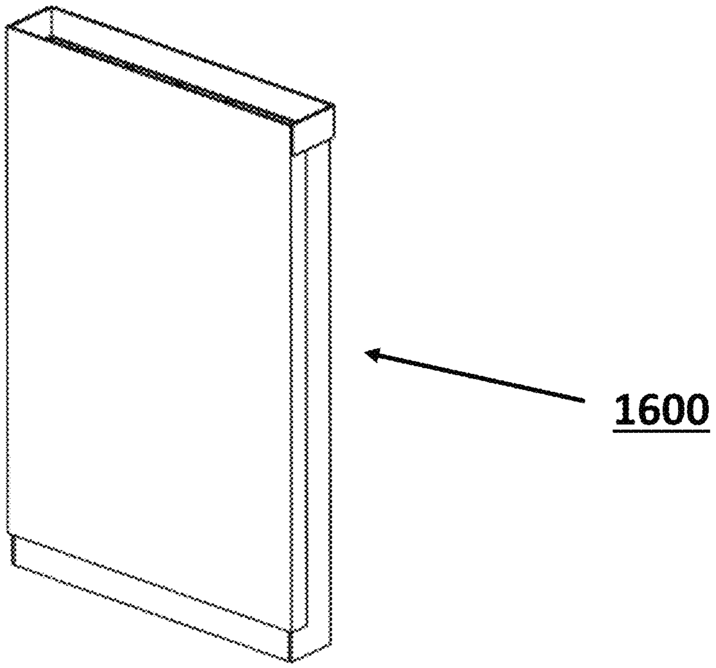

FIGS. 16A and 16B illustrate a wall assembly utilizing the wall surface 1300 (see FIG. 13) and the front wall surface 1500 (see FIG. 15), both before and after the wall is completely assembled.

Fog exits the fog-generating device (e.g., the atomization chamber 102 of FIG. 1), enters the wall assembly along a bottom surface then travels up the wall while encountering the redirectors 1301 (see FIG. 13) along its path until the fog exits the wall assembly 1600 along a top surface thereof.

Figure 17A:
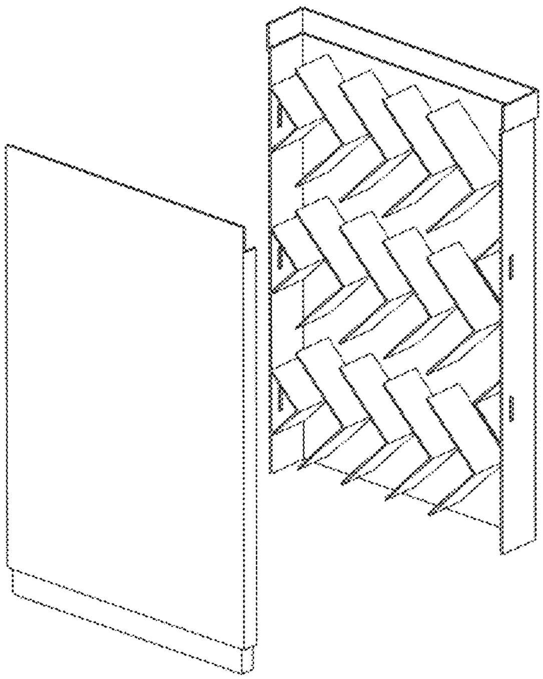
Figure 17B:
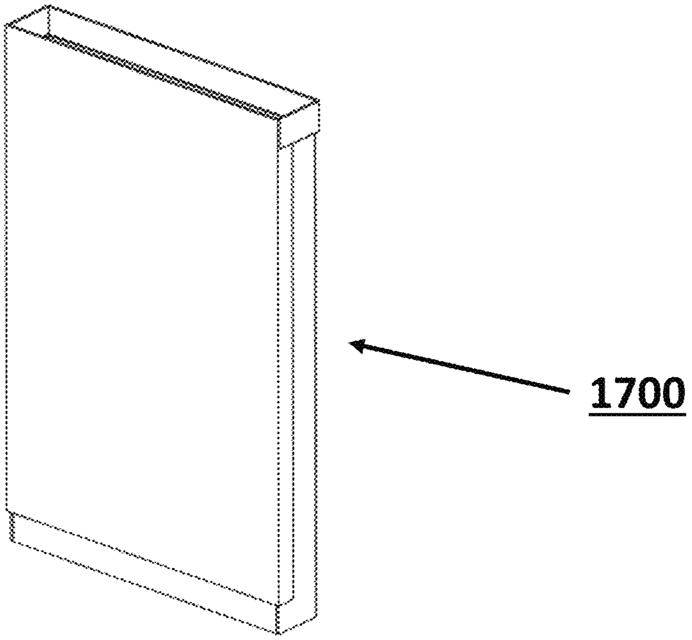

FIGS. 17A and 17B illustrate a wall assembly utilizing the wall surface 1400 (see FIG. 14) before and after the complete wall is assembled. Fog exits the atomization chamber, enters the wall assembly along a bottom surface then travels up the wall while encountering the redirectors 1401 (see FIG. 14) along its path until the fog exits the wall assembly 1700.

Figure 18A:
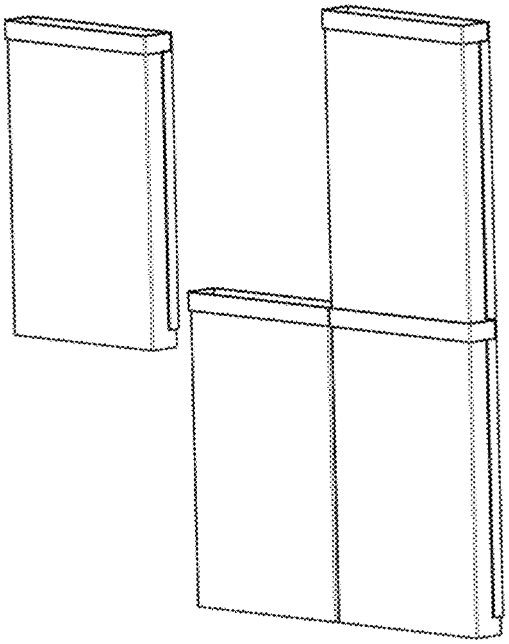
FIGS. 18A and 18B depicts multiple wall with redirectors embedded in the assemblies as depicted in FIGS. 16B and 17B joined together to provide a larger fog flow path channel.
Figure 18B:
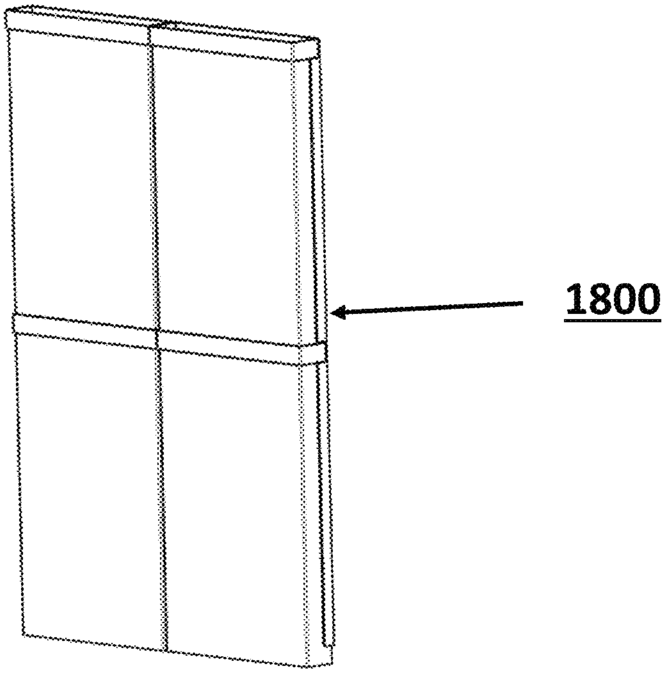

FIGS. 18A and 18B illustrates how multiple wall assemblies 1600 (see FIG. 16B) or 1700 (see FIG. 17B) may be joined together to create a larger and wider wall 1800 including the inventive redirectors of the present invention. The multi-section wall assembly 1800 can comprise only a wall surface 1600 (FIGS. 16A and 16B) or only a wall surface 1700 (FIGS. 17A and 17B) or the two different wall surfaces can be intermixed. This arrangement can be utilized on larger fogging units where an extended tube protruding above the unit is undesirable.

FIGS. 19A and 19B illustrate another embodiment of the invention where the redirectors are contained in a multi-channel, somewhat rectangular/oval cross-section tube. This redirector arrangement employs the redirectors in a more robust external arrangement and creates multiple dedicated channels for fog to travel as it exits the atomization chamber in route to the area being treated.

The assembly is designed so that it can be secured to an adjacent structure, such as a post, a wall, an interior side of a van or transport vehicle or to a bulkhead in an aircraft. The design is easily scalable and can be utilized where even extremely high volumes of airflow are desirable. Both the shape of the tube and the added infrastructure created by multiple interior channels optimize this design for rugged environments where the tube may be exposed to occasional contact with equipment or persons moving about the equipment.

FIG. 19A illustrates a single segment 1901 of this multi-channel rectangular/oval tube 1900. The section has both a male end 1908 and a female end 1909, so that individual sections can be easily linked together.

The segment 1901 comprises multiple isolated channels 1902 which serve as the pathway through which the fog travels as it moves from the atomization chamber (in an embodiment employing a sonic transducer of FIG. 1) to the treated space. Each turn or bend within the tube 1900 serves as a redirector 1901 that creates a collision point for larger particles to collect and then drain back down into the atomization chamber.

FIGS. 19B and 19C illustrate multiple segments 1901 assembled to form an assembly 1900, highlighting a male end 1908 of one segment attached to a female end 1909 of an adjacent segment, to complete the assembly.

Fog exits the atomization chamber, enters the assembly 1900 at location 1906 and travels up the tube encountering the redirectors 1901 along its path. Along the path, larger particles collide with the redirectors while smaller particles do not, thereby allowing the smaller particles to be introduced to the environment as they exit the tube at location 1907.

The number of redirector segments 1901 utilized to create a full assembly 1900 is determined by the end user and the intended application.

Increasing the number of redirector segments 1901 reduces the median particle size introduced to the environment, ensuring that small particles are not overwhelmed by larger ones and are available to perform their designated task.

Reducing the number of redirector segments 1901 allows for a slightly higher volume fog production but is less efficient at ensuring larger particles are eliminated from the fog droplet path airflow as they travel through the invention from bottom to top of the wall.

Figure 20A:
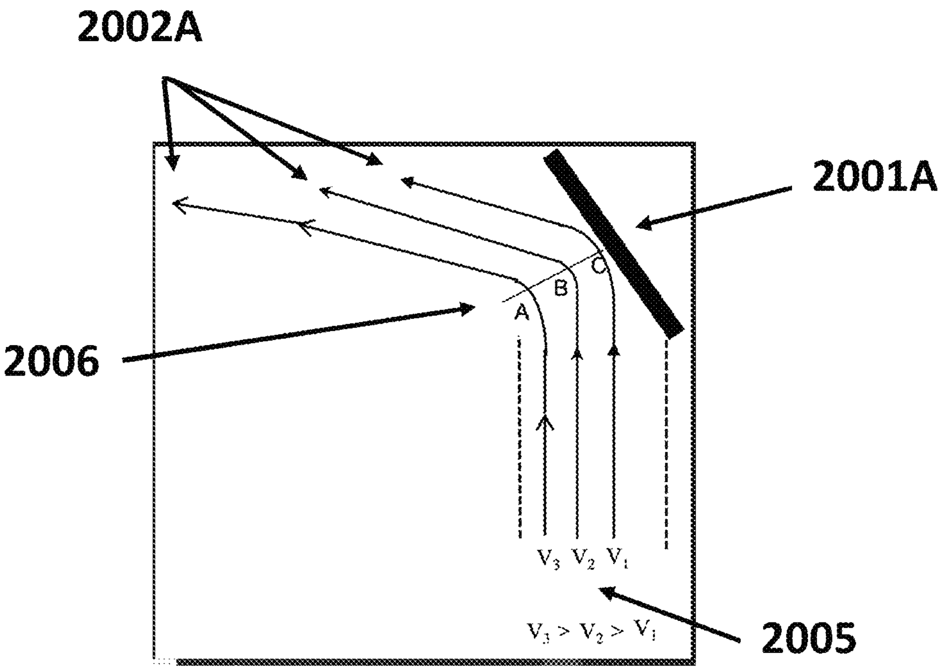
FIGS. 20A and 20B depict redirector surfaces and representations of fog droplets interacting therewith.
Figure 20B:
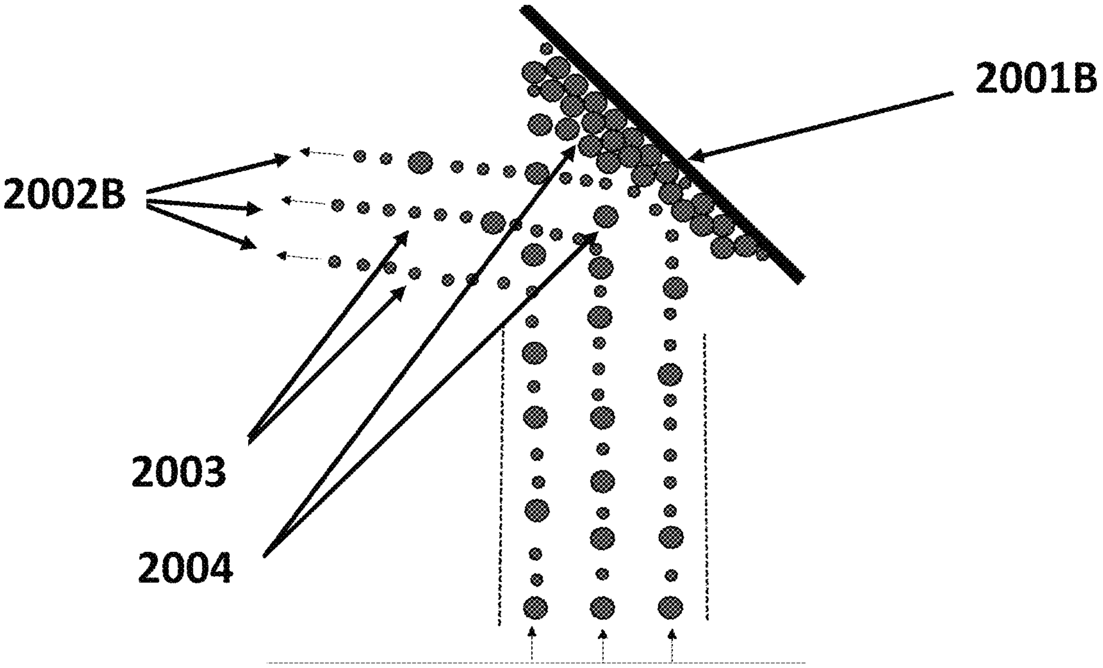

FIGS. 20A and 20B illustrate the functional aspects of the invention to assist in better understanding how the use of redirectors eliminates larger particle droplets from the flow stream, while allowing smaller droplets to pass by the redirectors eventually exiting the flow channel(s).

FIG. 20A illustrates vectors $V_3$, $V_2$, and $V_1$ 2005. Bernoulli's equation provides the pressure along a streamline. The pressure gradient along the line ABC 2006 has a higher pressure at point C, a pressure at point B lower than at point C and a pressure at point A lower than at point B. The pressure gradient creates a force pushing the particles away from the redirector 2001A allowing smaller particles to flow within the redirected streamline 2002A.

FIG. 20B illustrates how larger particles exit the flow stream 2002B and collect on a redirector 2001B. Particles with low inertia are required to follow rapidly changing flow conditions—such as changing flow 2002B created by a redirector 2001B The inertia or mass of the smaller particles 2003 is sufficiently small for it to follow the streamlines 2002B.

The inertia or mass of the larger particles 2004 is sufficiently large to cause little or no conformity to the changing flow pattern 2002B created by the redirector 2001B as they encounter the force created by the pressure gradient and collide with the redirector 2002B.

Thus, particles with a small inertia 2003 are expected to follow the flow stream 2002B that is deflected by the redirector 2001B and particles with a large inertia 2004 are expected to deposit out of the droplet stream rapidly as they pass through the pressure gradient and collide with the redirector 2001B.

While some larger particles are able to avoid colliding with a single redirector and remain in the stream, utilizing a series of redirectors in a flow stream ensures that enough larger particles are eliminated to meet the expectations of the invention.

What is claimed is:

1. A structure for receiving fog particles from a fog-producing device, the structure comprising:

a tubular body defining a hollow interior and a first and a second opposing open ends, the first and second open ends providing access to the hollow interior, the first open end for attaching to the fog-producing device and for receiving fog particles therefrom;

a plurality of spaced-apart redirectors mounted on opposing surfaces of a relatively planar substrate, the substrate and the plurality of spaced-apart redirectors disposed within the hollow interior, the plurality of spaced-apart redirectors arranged to create nonlinear fog flow pathways on the opposing surfaces, fog particles travel along nonlinear fog flow pathways on the opposing surfaces as the plurality of spaced-apart redirectors repeatedly after a direction of fog flow and fog flow does not reverse direction between the first and second open ends, fog particles-striking or passing proximate the plurality of spaced-apart redirectors, wherein fog particles of a first size having a first inertia follow nonlinear fog flow pathways and exit the structure at the second open end for treating a target, and fog particles of a second size having a second inertia collide with a redirector, fall out of nonlinear fog flow pathways, and do not exit the structure at the second open end, wherein a first size is smaller than a second size and a first inertia is less than a second inertia.

2. The structure of claim 1, wherein each one of the plurality of spaced-apart redirectors presents a barrier in fog flow pathways, requiring fog to change direction upon striking or passing proximate a redirector surface.

3. The structure of claim 1, wherein the structure acts upon fog particles such that fog particles exiting the structure at the second open end have a median diameter of 0.6 microns, and a majority of fog particles exiting the structure at the open end are less than 2.5 microns in diameter.

4. The structure of claim 1, wherein the structure acts upon fog particles such that 98% of fog particles exiting the structure at the second open end are less than 2.5 microns in diameter.

5. The structure of claim 1, wherein the structure acts upon fog particles such that a majority of fog particles exiting the structure at the second open end are less than 5 microns in diameter.

6. The structure of claim 1, wherein fog particles comprise only water or water and an active substance capable of being aerosolized.

7. The structure of claim 6, wherein an active substance comprises an insecticide, a nutrient solution, a decontaminating solution, a parasitic solution, a contaminant, a neutralizing solution, a deactivating solution, a deodorizing solution, or a disinfectant.

8. The structure of claim 1, wherein each one of the plurality of spaced-apart redirectors comprises a flat planar surface, a solid surface, a mesh surface, or a honey-comb surface.

9. The structure of claim 1, wherein a first edge of a first group of the plurality of spaced-apart redirectors is affixed to a first surface of the substrate and an opposing second edge of the first group of the plurality of spaced-apart redirectors defines a shape complementary to a shape of an inside surface of the tubular body, wherein a first edge of a second group of the plurality of spaced-apart redirectors is affixed to an opposing second surface of the substrate and an opposing second edge of the second group of the plurality of spaced-apart redirectors defines a shape complementary lo a shape of an inside surface of the tubular body.

10. The structure of claim 1, wherein the fog flow pathways comprise nonlinear fog flow pathways as determined by placement of each one of the plurality of spaced-apart directors.

11. The structure of claim 1, wherein the structure acts upon fog particles and foo particles exiting the structure al the second open end are directed at a target comprising a material surface, an enclosed space, a hard surface, a porous surface, a fabric, air within an enclosed space, and cracks and crevices within a material surface.

12. The structure of claim 1, wherein increasing a number of the plurality of spaced-apart redirectors decreases a number of fog particles of the second size exiting the structure at the second open end and reduces a volume of fog exiting the structure at the second open end.

13. The structure of claim 1, wherein a cross section of the tubular body is circular.

14. The structure of claim 1, wherein increasing a velocity of fog particles traveling in the fog flow pathways decreases a number of particles of the second size exiting the structure at the second open end, and wherein decreasing a velocity of fog particles traveling in the fog flow pathways increases a number of particles of the second size exiting the structure at the second open end.

15. The structure of claim 1, wherein varying a velocity of fog particles traveling in the fog flow streamline paths changes a ratio of particles of the first size to particles of the second size exiting the structure at the second open end, and wherein varying an orientation of the plurality of spaced-apart redirectors changes a ratio of particles of the first size to particles of the second size exiting the structure at the second open end.

16. An assembly comprising:

a first tube comprising a first end and a second end;

a second tube comprising a first end and a second end, wherein the first end of the second tube is connected to the second end of the first tube;

a first insert positioned within the first tube, said first insert comprising;

a first substrate having a first end and a second opposing end, a first axis defined between the first end and the second end of the first substrate;

a first plurality of redirectors attached to both opposing surfaces of the first substrate and spaced apart from the first end to the second end of the first substrate;

one or more tabs configured to operatively engage mating elements within the first tube to lock the first insert in place within the first tube;

wherein consecutive redirectors of the first plurality of redirectors from the first end to the second end of the first substrate are oriented at different angles relative to the first axis;

wherein the first insert has a width and length for insertion into the first tube, wherein free edges of the first plurality of redirectors shaped to fit within the first tube such that a shape of the free edges of each one of the first plurality of redirectors is complementary to a shape of the inside surface of the first tube;

a second insert positioned within the second tube, said second insert comprising;

a second substrate having a first end and a second opposing end and a second axis defined between the first end and the second end of the second substrate;

a second plurality of redirectors attached to both surfaces of the second substrate and spaced apart from the first end to the second end of the second substrate;

one or more tabs configured to operatively engage mating elements within the second tube to lock the second insert in place within the second tube;

wherein consecutive redirectors of the second plurality redirectors from the first end to the second end of the second substrate are oriented at different angles relative to the second axis;

wherein the second insert has a width and length for insertion into the second tube wherein free edges of the second plurality of redirectors shaped to fit within the second tube such that a shape of the free edges of each one of the second plurality of redirectors is complementary to a shape of the inside surface of the second tube;

wherein the first end of the first tube is configured to receive a first flow of fog exiting an exit tube of a fog generating device, said first flow of fog comprising particles having a range of sizes;

wherein the first plurality of redirectors attached to both surfaces of the first substrate are configured to repeatedly alter a direction of flow of fog within the first tube into a zig-zag pattern on both surfaces of the first substrate and further configured to provide collision points with particles having a size above a large particle threshold;

wherein the second plurality of redirectors attached to both surfaces of the second substrate are configured to repeatedly alter a direction of flow of fog within the second tube into a zig-zag pattern on both surfaces of the second substrate and further configured to provide collision points with particles having a size above a large particle threshold;

wherein the second end of the second tube is configured to direct a second flow of fog to an area to be treated, wherein the second flow of fog has a reduced number of particles having a size above the large particle threshold relative to the first flow of fog.

17. The assembly of claim 16, wherein the plurality of redirectors of the first insert and the second insert are oriented at an angle of about 45 degrees relative to the axis of the respective first insert and the second insert.

18. The assembly of claim 16, wherein nonconsecutive redirectors of both the first and second plurality of redirectors from the first end to the second end of the respective first and second inserts are oriented about parallel to each other in both the first and second inserts.

19. The assembly of claim 16, wherein the second end of the first tube comprises one of a male or female connector, and wherein the first end of the second tube comprises another one of the male or female connector such that the first end of the second tube is configured to matingly engage the second end of the first tube.

20. The assembly of claim 16, wherein the large particle threshold is about 2.5 microns.

21. The assembly of claim 16, wherein:

the first substrate of the first insert extends from the first end to the second end of the first tube upon positioning the first insert within the first tube; and the second substrate of the second insert extends from the first end to the second end of the second tube upon positioning the second insert within the second tube.

* * * * *